(12) United States Patent
Pera et al.

(10) Patent No.: US 8,119,774 B2
(45) Date of Patent: Feb. 21, 2012

(54) CELL MARKER FOR HEPATIC AND PANCREATIC STEM CELLS AND PROGENITOR CELLS

(76) Inventors: Martin Pera, Prahran (AU); Susan Hawes, Mentone (AU); Lincon Stamp, Southbank (AU); Heather Crosby, Birmingham (GB); Alastair Strain, Birmingham (GB)

( * ) Notice: Subject to any disclaimer, the term of this patent is extended or adjusted under 35 U.S.C. 154(b) by 325 days.

(21) Appl. No.: 10/574,885

(22) PCT Filed: Oct. 8, 2004

(86) PCT No.: PCT/AU2004/001376
§ 371 (c)(1), (2), (4) Date: Mar. 14, 2007

(87) PCT Pub. No.: WO2005/033126
PCT Pub. Date: Apr. 14, 2005

(65) Prior Publication Data
US 2007/0218059 A1    Sep. 20, 2007

(30) Foreign Application Priority Data
Oct. 9, 2003  (AU) .............................. 2003905516

(51) Int. Cl.
C07K 16/00 (2006.01)
C12N 5/00 (2006.01)
(52) U.S. Cl. ..................... 530/388.1; 435/346
(58) Field of Classification Search ............. None
See application file for complete search history.

(56) References Cited

U.S. PATENT DOCUMENTS
4,281,061 A  *  7/1981  Zuk et al. ................ 435/7.9

FOREIGN PATENT DOCUMENTS
WO         01/98463 A1     12/2001
WO     WO 01/98463    *   12/2001
WO     WO 03/040355   *    5/2003
WO     WO 03 040355        5/2003

OTHER PUBLICATIONS

Schopperle et al BBRC, 2003, pp. 285-290).*
Bost et al., Immuno. Invest. 1988 ;17:577-586.*
Emerson et al( Blood, 1989, v.74, pp. 49-55).*
Workshop on the Basic Biology of Mammalian Stem Cells, National Institute of General Medical Sciences, National Institutes of Health, Jun. 9-10, 2002, Pooks Hill Marriott, Bethesda, Maryland.
Pera, et al., "Analysis of Cell-Differentiation Lineage in Human Teratomas Using New Monoclonal Antibodies to Cytostructural Antigens of Embryonal Carcinoma Cells," *Differentiation* 39(2):139-49 (1988).
Stamp et al., "A Novel Cell-Surface Marker Found on Human Embryonic Hepatoblasts and a Subpopulation of Hepatic Biliary Epithelial Cells," Stem Cells 23:103-12 (2005).
Supplemental European Search Report for European Patent Application No. EP04761409 (Sep. 8, 2008).
Terai, "Development of New Regenerative Model: Transplanted GFP Positive Bone Marrow Cell Migrated Into Damaged Area and Differentiated Into Hepatocyte," Hepatogogy 34(4):235A (2001).
Yamamoto et al, "Differentiation of Embryonic Stem Cells Into Hepatocytes: Biological Functions and Therapeutic Application," Hepatology 37(5):983-93 (2003).
Forbes et al., "Hepatic Stem Cells," J Pathol 197:510-518 (2002).
Office Action from the European Patent Office (EPO) for European Patent Application No. EP04761409 (Aug. 12, 2011).

* cited by examiner

Primary Examiner — Michail Belyavskyi
(74) Attorney, Agent, or Firm — Nixon Peabody LLP

(57) ABSTRACT

The present invention provides a cell marker that is characterized by binding to a GCTM-5 antibody of active fragment. The cell marker identifies a unique sub-population of stem cells that show characteristics of hepatic or pancreatic stem cells or hepatic or pancreatic progenitor cells. More specifically the marker is an early liver marker, which could prove a useful tool for the isolation and identification of liver and pancreatic progenitors for both diseased adult liver and differentiating human embryonic stem cells.

13 Claims, 13 Drawing Sheets ary). Magnification ×200. C, pancreas stained with GCTM-5. Magnification ×200.

CELL MARKER FOR HEPATIC AND PANCREATIC STEM CELLS AND PROGENITOR CELLS

This application is a national stage application under 35 U.S.C. §371 from PCT Application No. PCT/AU2004/001376, filed Oct. 8, 2004, which claims the priority benefit of Australian Application No. 2003905516, filed Oct. 9, 2003.

The present invention relates to a cell surface marker, and to an antibody which binds to the cell surface marker and uses thereof. The invention also relates to cells isolated using the cell surface marker and antibody and uses thereof.

BACKGROUND TO THE INVENTION

It is now widely anticipated that advances in stem cell biology and biotechnology will lead to the development of cell-based therapy for many disorders, including degenerative diseases of the liver. Interconversion between the hepatic and pancreatic endodermal lineages may facilitate the use of hepatogenic stem cells from adult or embryonic sources offering potential for cell based transplantation therapy of diseases of either of these closely related tissues. However, controversy exists over the nature of the stem cell or stem cells that repopulate the adult liver following various forms of injury. Given the uncertainty over the precise nature of the progenitor cells in the hepatic lineage, the isolation of a suitable cell type for transplantation remains problematic, as does selection and expansion of precursor cells from embryonic stem cell populations, or ex-vivo expansion of progenitors from foetal, neonatal or adult sources. Without the ability to identify particular hepatic endodermal stem cells, it is difficult to study these cells in isolation and to use them for the development of pharmaceuticals that might influence liver cell growth and differentiation, or the transdifferentiation of these cells into other lineages, including pancreatic.

Thus the present invention provides reagents and methods useful in identifying and isolating sub-populations from stem cell populations such as hepatic stem cells that may be used in repopulating liver or other endodermal tissues including pancreas.

SUMMARY OF THE INVENTION

The present invention provides a cell marker which is characterized by binding to a GCTM-5 antibody of active fragment. The antibody may in turn be used to detect the cell and to isolate cells expressing the marker.

The cell marker of the present invention identifies a unique sub-population of stem cells that preferably show characteristics of hepatic or pancreatic stem cells or hepatic or pancreatic progenitor cells. More specifically the marker is an early liver marker, which could prove a useful tool for the isolation of liver and pancreatic progenitors for both diseased adult liver and differentiating human embryonic stem cells. Liver and pancreas are embryonically linked and they can interconvert through transdifferentiation. Hence the marker can be found on hepatic and pancreatic cells and progenitor cells. More preferably the marker can be found on hepatoblasts that can differentiate to a liver, hepatic or pancreatic cell and cells of the biliary epithelium.

The marker and antibody may be used to isolate these cells as isolated cells or subpopulations and use them for the treatment of liver and/or pancreatic conditions.

The marker and the antibody may be used to diagnose and to treat hepatic and pancreatic malignancies. By the expression of the GCTM-5 antigen or epitope on the cell surface, and the release of the antigen to the media, these components are useful as tools for monitoring the presence of liver and pancreatic stem cells.

The invention also provides compositions and kits including the antibody and use of the marker for the isolation and identification of cell populations which are preferably hepatic or pancreatic stem cells or progenitor cells.

DETAILED DESCRIPTION

Figure 1A:
FIG. 1 shows immunostaining revealing GCTM-5 expression in GCT27X-1 embryonal carcinoma cells. (A) shows a brightfield image of GCT27X-1 morphology and density, and (B) shows the rare expression of GCTM-5. Magnification 400×.

In a first aspect of the present invention there is provided a cell marker said marker characterized by binding to a GCTM-5 antibody or an active fragment thereof. The cell surface marker or the antigen or epitope identified by the GCTM-5 antibody may be a polypeptide which migrates in an SDS-PAGE gel with an apparent molecular weight of 50 kDa. Preferably the marker includes a GCTM-5 epitope or equivalent. More preferably the stem cell marker is a marker of cells of the biliary epithelium or luminal bile duct or the pancreatic duct. Preferably the marker is a marker of hepatic, pancreatic or endodermal stem cells.

The stem cell marker of the present invention identifies a unique sub-population of stem cells that preferably show characteristics of hepatic or pancreatic stem cells or hepatic or pancreatic progenitor cells. More specifically the marker is an early liver marker, which could prove a useful tool for the isolation of liver and pancreatic progenitors for both diseased adult liver and differentiating human embryonic stem cells. Liver and pancreas are embryonically linked and they can interconvert through transdifferentiation. Hence the marker can be found on hepatic and pancreatic cells and progenitor cells. More preferably the marker can be found on hepatoblasts that can differentiate to a liver, hepatic or pancreatic cell and cells of the biliary epithelium.

The marker is an antigen of GCTM-5 antibody or fragment thereof and by virtue of the binding the marker includes a GCTM-5 epitope or equivalent. More preferably, the marker is a cell surface marker.

The cell surface marker binds to a GCTM-5 antibody. More preferably the GCTM-5 antibody is produced by a hybridoma having an ECACC accession number 03101603.

The marker may be isolated using affinity techniques or other means of protein purification or by expression cloning or other techniques known by those skilled in the art.

In a another aspect of the present invention there is provided a detector of a cell type which identifies a marker on the cell type said marker characterized by binding to a GCTM-5 antibody or active fragment thereof. Preferably, the detector is an antibody or active fragment thereof Applicants have found that an antibody GCTM-5 antibody can identify a subpopulation of cells which show characteristics of a hepatic or pancreatic stem cell. The antibody detects a marker on the cell type that is indicative of this cell type. Accordingly, the present invention includes any detector that can detect the marker that is identified by the GCTM-5 antibody or an active fragment thereof. The marker will therefore include some or all of the epitope that the GCTM-5 antibody reacts with. However, providing there is some of the epitope or an equivalent, it will be sufficient for the detector to identify the cell type. Hence it is within the scope of the present invention that the detector is any molecule that can recognise the same marker that is identified by GCTM-5 antibody or an active fragment thereof.

Accordingly, a "GCTM-5 epitope" as used herein is any molecule that can be identified by GCTM-5 antibody or an active fragment thereof and includes active portions of the epitope that can bind to the GCTM-5 antibody or an active fragment thereof.

The "equivalent" as used herein with respect to the antigen, epitope or marker is a molecule that can elicit a binding or recognition by the GCTM-5 antibody or active fragment thereof. Therefore, it too can be identified by GCTM-5 antibody but may not be the exact epitope of GCTM-5. It may be a portion of the epitope. The equivalent may have mutations that do not substantially affect the binding or recognition by GCTM-5 antibody. Due to the stringency of the binding, equivalents can be identified which are partially identified by GCTM-5 antibody and therefore bind weakly to the antibody. Accordingly, where the "marker" or "antigen" that is identified by GCTM-5 antibody is referred to, this includes equivalents to those molecules as described above.

A "detector" as used herein may be any form of detector and may include antibodies or fragments, ligands or any complimentary molecule that identifies and locates a marker that can be identified by the GCTM-5 antibody.

A "fragment" or "active fragment" as used herein with respect to the antibody includes any antibody fragments containing functional portions thereof. The term "antibody" includes any monospecific or bispecific compound comprised of a sufficient portion of the light chain variable region and/or the heavy chain variable region to effect binding to the epitope to which the whole antibody has binding specificity. The fragments can include the variable region of at least one heavy or light chain immunoglobulin polypeptide, and include, but are not limited to, Fab fragments, F(ab')$_2$ fragments, and Fv fragments.

Throughout the description and claims of this specification the word "comprise", and variations of the word such as "comprising" and "comprises", is not intended to exclude other additives or components or integers or steps.

In a preferred aspect, the present invention provides a detector of a cell type which identifies a marker on a subpopulation of stem cells said marker characterized by binding to a GCTM-5 antibody or active fragment thereof. Preferably, the detector is a GCTM-5 antibody or active fragment thereof.

The present invention provides a detector of a cell type which can be used to identify a unique sub-population of stem cells which show characteristics of a hepatic or pancreatic stem cell. More preferably, the sub-population of stem cells is a hepatic progenitor cell. Even more preferably, the cells are proliferating hepatic progenitor cells. Most preferably the cells are hepatoblasts.

The term "hepatic stem cell" may be used interchangeably with "liver stem cell" and encompasses within its scope a hepatoblast, an embryonic liver foetal cell, liver or hepatic progenitor cells or biliary cells, preferably biliary epithelial cells. Most preferably these cells have the capacity to proliferate in the liver. More preferably, the hepatic stem cell is a hepatoblast. The hepatoblast is a multi-potential cell which has the capacity to differentiate to hepatocytes, biliary cells or pancreatic cells. It is now found that the cells identified by the antibody, preferably GCTM-5 antibody or fragment thereof can identify this cell type which has the propensity to differentiate into liver, hepatic or pancreatic cells and especially cells that are actively proliferating. This is evidenced by strong GCTM-5 antibody recognition of cells found in diseased regenerating tissue. The possible interconversion between liver and pancreatic cells shows that the antibody is capable of being used to identify potential pancreatic cells as well as liver cells.

The staining patterns of GCTM-5 antibody on the stem cells suggest that the antibody will be a useful marker for distinguishing between extraembryonic and embryonic endodermal cells. This is evidenced by an absence of significant reactivity of GCTM-5 antibody with yolk sac carcinoma cell lines or with yolk sac.

Preferably, where the detector is an antibody, then the antibody may be a monoclonal or polyclonal antibody, a recombinant antibody or an active fragment thereof of an antibody that can still bind and detect the marker. Preferably, the antibody is any antibody specific for a marker identified by a GCTM-5 antibody or a fragment thereof. The antibody of the present invention encompasses any antibody or fragment thereof, either native or recombinant, synthetic or naturally-derived, monoclonal or polyclonal which retains sufficient specificity to bind specifically to the marker or a fragment thereof which is indicative of an antigen identified by a GCTM-5 antibody or an active fragment thereof.

A recombinant antibody can be produced by any recombinant means known in the art. Such recombinant antibodies include, but are not limited to, fragments produced in bacteria and non-human antibodies in which the majority of the constant regions have been replaced by human antibody constant regions. In addition, such "humanized" antibodies can be obtained by host vertebrates genetically engineered to express the recombinant antibody.

The antibodies or active fragments thereof may be obtained by methods known in the art for production of antibodies or functional portions thereof. Such methods include, but are not limited to, separating B cells with cell-surface antibodies of the desired specificity, cloning the DNA expressing the variable regions of the light and heavy chains and expressing the recombinant genes in a suitable host cell. Standard monoclonal antibody generation techniques can be used wherein the antibodies are obtained from immortalized antibody-producing hybridoma cells. These hybridomas can be produced by immunizing animals with HSCs or progeny thereof, and fusing B lymphocytes from the immunized animals, preferably isolated from the immunized host spleen, with compatible immortalized cells, preferably a B cell myeloma.

The antibodies or active fragments thereof may be obtained from any source. Effectively, any means which detects or identifies the presence of a marker identified by GCTM-5 antibody or fragments of the marker on the cells is within the scope of the present invention. Most preferably, it is an antibody. More preferably, it is a GCTM-5 antibody.

The marker is any molecule or antigen on the sub-population of stem cells which is indicative of the sub-population of stem cells. Preferably, it is indicative of a hepatic stem cell. More preferably it is a marker of a cell of the biliary epithelium or luminal bile duct or pancreatic ducts, or it is a hepatic or pancreatic progenitor cell or a hepatoblast. More preferably it is a hepatoblast. More specifically, the cell is proliferating. The molecule indicative of the marker may be an epitope or a portion of an epitope or equivalent that can be identified by the GCTM-5 antibody or an active fragment of the antibody that is functionally the same as the whole GCTM-5 antibody. The marker may also be identified by a detector which may be a polyclonal antibody which also recognises the epitope defined by the GCTM-5 antibody or a functionally active fragment thereof or it may be any ligand which can attach to the marker identified by the GCTM-5 antibody. Hence the marker will include a GCTM-5 epitope, a portion or equivalent of the epitope sufficient to elicit a recognition or detection by GCTM-5 antibody. The marker may be larger than the epitope. However, it will contain sufficient GCTM-5 epitope to elicit the recognition by GCTM-5 antibody or an active fragment thereof.

Preferably, the marker is further characterized by a polypeptide with an apparent molecular weight of 50 kDa as determined on an SDS-PAGE gel.

The detector and a GCTM-5 antibody will recognise the same epitope or molecule including the GCTM-5 epitope or equivalent. The detector can be tested for its suitability to detect the marker by its ability to compete against the GCTM-5 antibody for the marker.

The preferred antibody is GCTM-5 antibody which is a monoclonal antibody which was raised against a membrane preparation from a testicular seminoma tumour. Surprisingly, screening of this reagent against a pluripotent human embryonal carcinoma cell line revealed that it bound to a minority cell population in the culture that was unreactive with markers of pluripotent stem cells. GCTM-5 antigen is now found to be expressed exclusively in the foetal liver of a seven week human foetus. Concurrent experimentation on normal and diseased human liver tissue revealed an expression localised to the ductal region and more specifically to a subpopulation of cells within the biliary epithelium The present invention also provides a hybridoma which produces a GCTM-5 antibody or an antibody to the marker that is characterized by its binding to the GCTM-5 antibody. Preferably, the hybridoma has a European Collection of Animal Cell Cultures (ECACC) accession number 03101603 which was deposited on 16 Oct. 2003.

In another aspect of the invention, there is provided a method of identifying a sub-population of stem cells in a cell sample, said method comprising
identifying the stem cells which express a marker said marker characterized by binding to a GCTM-5 antibody or active fragment thereof.

The present invention has identified a marker which is indicative of a unique sub-population of stem cells. Preferably the sub population of stem cells are hepatic or pancreatic stem cells or ductal cells. Preferably the sub-population of hepatic stem cells includes hepatoblasts, embryonic liver foetal cells, liver or hepatic progenitor cells, biliary cells, biliary epithelial cells, multi-potential cells which can differentiate to hepatocytes, biliary cells and pancreatic cells and cells of the luminal surfaces of biliary ducts or pancreatic ducts, or other cell types of endodermal origin. Preferably the hepatic stem cells are hepatic and liver progenitor cells which have the capacity to proliferate. More preferably, the hepatic stem cell is a hepatoblast. Therefore, the method is useful for identifying hepatic progenitor cells rapidly proliferating and differentiating in liver cancers and normal liver tissue. The subpopulation also contains pancreatic stem or progenitor cells.

The cell sample may be from any source of biological material, but is not limited to, blood, tissues, sputum, urine, and faecal samples. The cells may also be cell cultures which include progenitor cells such as, but not limited to, an embryonic stem (ES) cell culture or human embryonic stem (HES) cell culture of undifferentiated cells or pluripotent stem cells or any hepatic cell culture which includes adult and foetal or undifferentiated liver or hepatic cells. The cell sample may be a diseased liver sample including hepatic stem cells. The cell sample may be any type of tissue cell obtained directly from embryonic, fetal or adult sources or after cultivation or manipulation in vitro including manipulation to alter its differentiation potential. The cell sample may be any sample in which a cell surface is exposed for identification by the antibody or detector. The marker that is indicative of the subpopulation is a cell surface marker.

Preferably the cells are identified by a detector which identifies the marker. Preferably, the detector is an antibody. More preferably the antibody is GCTM-5 antibody. However, it should be appreciated that whilst the GCTM-5 antibody can recognise the marker that identifies the stem cells, any molecule which can recognise the same epitope or an equivalent or a portion thereof can be used as a detector. Once the marker is established, it can be used as a target for those cells of the subpopulation. Hence anything that can be directed to identify the target or marker is within the scope of the present invention.

The marker as herein described is a marker that binds to a GCTM-5 antibody and active fragment thereof. The marker is further characterized by its apparent molecular weight of 50 kDa as determined on an SDS-PAGE gel. Preferably, it contains a GCTM-5 epitope or equivalent and is a cell surface marker.

The cell sample may be contacted to the detector by exposing the sample to the detector. Methods known to the skilled addressee for immunohistochemistry using a detector such as an antibody which recognises an antigen may be employed. The use of primary and secondary antibodies to further enhance the identification can be employed.

To assist in identification of the cells identified by the detector, the detector can be conjugated to other suitable molecules and compounds including, but not limited to, enzymes, magnetic beads, colloidal magnetic beads, haptens, fluorochromes, metal compounds, radioactive compounds or drugs. The enzymes that can be conjugated to the detector include, but are not limited to, alkaline phosphatase, peroxidase, urease and β-galactosidase. The fluorochromes that can be conjugated to the detector include, but are not limited to, fluorescein isothiocyanate, tetramethylrhodamine isothiocyanate, phycoerythrin, allophycocyanins and Texas Red. The metal compounds that can be conjugated to the detector include, but are not limited to, ferritin, colloidal gold, and particularly, colloidal superparamagnetic beads. The haptens that can be conjugated to the detector include, but are not limited to, biotin, digoxigenin, oxazalone, and nitrophenol. The radioactive compounds that can be conjugated or incorporated into the antibodies are known in the art, and include but are not limited to technetium 99m, $^{125}$I and amino acids comprising any radionuclides, including, but not limited to $^{14}$C, $^{3}$H and 35S.

In a preferred embodiment there is provided a method of identifying a further subpopulation of stem cells, said method comprising subjecting the cells which express a marker said marker characterized by binding to GCTM-5 antibody or an active fragment thereof to further markers selected from the group including N-CAM, HEA-125, CK-19, harmonin and Ep-CAM and selecting for reactivity of the cells to the further markers.

Further clarification of the GCTM-5 positive cells indicated that another subpopulation of cells exists within the GCTM-5 (+) cells that are negative for CK-19 or N-CAM, classical markers of ductal reactive cells. Hence the applicants have found a means to identify another sub-population of cells based on expression of a GCTM-5 antigen or equivalent which is identified by the antibody GCTM-5 and a further subpopulation of cells that are GCTM-5 (+), CK-19 (−) and N-CAM (−). This suggests that GCTM-5 will be a useful reagent for defining cell lineage relationships between putative progenitor populations in embryonic liver and the biliary epithelium during tissue repair. Accordingly cells that are positive for CK-19 and N-CAM will also indicate further sub-populations of ductal cells.

The marker and the detector of the marker therefore provides reagents with particularly valuable properties and applications such as the identification of specific populations of cells, preferably, hepatic and pancreatic stem cells. Given the expression pattern of the GCTM-5 antigen, such populations of cells may include particular populations of stem cells such as liver or hepatic stem cells or bipotential liver/pancreatic stem cells such as hepatoblasts. The use of GCTM-5 antibody in combination with markers of ductal cells can identify further subpopulations that show positive or negative expression of these markers.

In another preferred embodiment, the present invention provides a method of identifying a subpopulation of ductal stem cells, said method including subjecting cells which express a marker said marker characterized by binding to GCTM-5 antibody or an active fragment thereof to further markers selected from the group including N-CAM, HEA-125, CK-19, harmonin and Ep-CAM.

Additional markers of ductal cells can further separate subpopulations in the cells that are reactive to the GCTM-5 antibody. Whilst the reactivity is indicative of biliary cells and biliary epithelial cells, preferably hepatoblasts, more preferably hepatic or pancreatic cells, the additional markers can identify cell populations that may be precursors of hepatic or pancreatic cells.

Therefore, it is preferred that the method identifies a subpopulation of pancreatic stem cells by subjecting the cells which express the marker said marker characterized by the binding of the GCTM-5 antibody or active fragment thereof to markers including harmonin or Ep-CAM. Harmonin is a pancreatic ductal marker. Preliminary staining of adult pancreatic tissue with the GCTM-5 antibody revealed an interesting pattern of expression. The antigen was absent from the endocrine portion of the pancreas (the islets), and from most of the exocrine tissue (the acinar cells, responsible for secretion of digestive enzymes). However, there was strong staining of areas corresponding to the pancreatic ducts. Colabelling of GCTM-5 positive cells with the pancreatic ductal marker harmonin confirmed the identity of the GCTM-5+ structures, though there were harmonin$^{+}$, GCTM-5$^{−}$ cells and harmonin$^{−}$GCTM-5$^{+}$ cells.

The present invention also provides for the use of GCTM-5 to identify subpopulations of cultured cells that have undergone genetic modification to incorporate lineage specific markers, such as green fluorescent protein under the control of a hepatic or pancreatic specific promoter.

In another aspect of the invention, there is provided a method of isolating a sub population of stem cells, said method comprising
   identifying the cells which express a marker said marker characterized by binding to a GCTM-5 antibody or active fragment thereof; and
   separating the cells identified by the marker.

By using the unique marker identified and described herein and which binds to the GCTM-5 antibody or active fragment thereof, the sub-population of cells that carry this marker can be isolated from the cell sample. It is preferred that the cell sample is a cell suspension which can facilitate the isolation and identification of the cells. However a cell culture on culture plates may be equally used and the identified cells isolated or "plucked" from the culture plate surface possibly for further culturing and expansion. Alternatively, cell suspensions or suspensions of aggregates of cells may be isolated from tissues including liver by methods such as those used in Example 4. The subpopulation of cells within a tissue that can react with the detector such as the antibody may be isolated by flourescence activated cell sorting, binding to superparamagnetic beads, panning etc.

Preferably the cells are isolated using a detector as herein described. Methods are available to the skilled addressee for isolating cells from a cell sample which utilise a detector such as an antibody. However, the present method utilises a unique marker which binds to a GCTM-5 antibody or another detector that recognises the same marker as GCTM-5 antibody or includes the GCTM-5 epitope or equivalent and a means to identify and isolate a sub-population from a stem cell population which have the propensity to differentiate to liver or pancreatic cells. Preferably the cell is a pancreatic, hepatic or liver stem cell. More preferably it is a liver progenitor cell. Most preferably the cell is a hepatoblast which has the capability of differentiating to a liver or pancreatic cell. Hence it is also preferred that the subpopulation of cells includes a pancreatic stem cell or pancreatic progenitor cell.

As herein described, the detector can be conjugated to suitable molecules, compounds and supports to facilitate the isolation of the cells by methods available to the skilled addressee. Some of the methods of isolating cells using detectors such as antibodies include, but are not limited to:
   capture methods where antibody bound to the surface of a cell allows the cell to be physically bound to a surface and thereby separated from other cells; and
   sorting methods, such as magnetic separation and fluorescence activated cell sorting, where a magnetic or fluorescent reagent is bound to the detector bound to the cell surface and separation is based on the magnetic or fluorescent properties of the cell.

GCTM-5 antibody is reactive with a cell surface epitope or a fragment of the epitope sufficient to react to the antibody, which provides the potential for this reagent to be used to isolate live cellular populations, by immunomagnetic separation, or by flow cytometry. Exploitation of stem cell populations, both adult and ES cell derived, for cell-based therapies is dependent upon isolation and characterisation of early precursor populations. GCTM-5 antibody or a detector that identifies the same marker identified by GCTM-5 antibody or the marker which includes a GCTM-5 epitope or equivalent can be a useful tool for the isolation of pancreatic, hepatic or liver stem cells from diseased adult or pediatric liver, normal foetal or embyonic liver, or normal pediatric or adult liver tissue.

In a preferred embodiment there is provided a method of isolating a further subpopulation of stem cells from a cell sample, said method comprising
   identifying the cells which express a marker said marker characterized by binding to a GCTM-5 antibody or active fragment thereof; and
   subjecting the identified cells to additional markers selected from the group including N-CAM, HEA-125, CK-19, harmonin and Ep-CAM; and
   separating the cells identified by the additional markers.

The subpopulation derived by the method may be positively or negatively selected based on the reaction to the markers N-CAM, HEA-125, CK-19, harmonin or Ep-CAM. These are markers of ductal cells. Preferably, the method isolates pancreatic precursors by identifying cells that are harmonin and/or Ep-CAM positive.

In combination with the techniques described herein, the present invention provides for the use GCTM-5 to select subpopulations of cultured cells that have undergone genetic modification to incorporate lineage specific markers, such as green fluorescent protein under the control of a hepatic or pancreatic specific promoter.

In another aspect of the present invention, there is provided a sub-population of cells which express a marker said marker characterized by binding to a GCTM-5 antibody or an active fragment thereof.

The present invention identifies and isolates a unique subpopulation of cells. Preferably it is a sub-population of stem cells. The subpopulation may comprise ductal cells. The cells that comprise the sub population may be selected from the group including hepatoblasts, embryonic liver foetal cells, liver or hepatic progenitor cells, biliary cells, biliary epithelial cells, multi-potential cells which can differentiate to hepatocytes, biliary cells and pancreatic cells and cells of the luminal surfaces of biliary ducts or pancreatic ducts. Preferably the hepatic stem cells are hepatic and liver progenitor cells that have the capacity to proliferate. The sub population is not necessarily a pure population of any particular cell type since any one of the above listed cells can express the marker. The sub-population may also represent cells of various degrees of differentiation. For instance, the cells may be multi-potential cells that can differentiate to hepatocytes, pancreatic cells or biliary cells or other endodermal cells. Accordingly, the sub population may comprise a mixture of these cells.

In a preferred embodiment, there is provided a further sub-population of stem cells which express a marker said marker characterized by binding to a GCTM-5 antibody or active fragment thereof and which cells are further identified by markers selected from the group including N-CAM, HEA-125, CK-19, harmonin and Ep-CAM.

The subpopulation of cells express the marker of the present invention. Due to differing reactivities of the various markers the cells can be divided into positively or negatively reacting cells. Preferably the subpopulation is a GCTM-5 (+) harmonin (+) or harmonin (−) subpopulation. More preferably the GCTM-5 (+) harmonin (+) cell is a pancreatic progenitor cell subpopulation. In another preferred embodiment, the subpopulation is GCTM-5 (+) Ep-CAM(+). These cells may be cells of the pancreatic lineage.

In yet another aspect of the present invention there is provided an isolated cell which expresses a marker said marker characterized by binding to a GCTM-5 antibody or active fragment thereof.

Preferably, the cell is identified by a detector which recognises a marker said marker characterized by binding to a GCTM-5 antibody or active fragment thereof. More preferably the cell is further identified by a marker selected from the group including N-CAM, HEA-125, CK-19, harmonin and Ep-CAM. Preferably the cell is a hepatic or pancreatic stem or progenitor cell.

In yet another aspect of the present invention, there is provided a method of culturing a hepatic or pancreatic stem cell, said method comprising
isolating the cells which express a marker, said marker characterized by binding to a GCTM-5 antibody or active fragment thereof; and
culturing the cells.

The present invention provides a method to identify a unique sub-population of cells which show characteristics of hepatic or pancreatic stem cells. These cells are identified by their expression of the marker of the present invention. Once identified and isolated these cells can be cultured to hepatic or pancreatic stem cells or preferably further differentiated to progeny of the hepatic stem cells, which may differentiate to liver, hepatic or pancreatic cells.

The cell sample and methods of isolation may be as herein described. Preferably the cells are isolated and identified using additional markers such as N-CAM, HEA-125, CK-19, harmonin and Ep-CAM. More preferably the markers such as harmonin and Ep-CAM are used to identify the pancreatic stem cells or cells of a pancreatic lineage.

Accordingly in another aspect there is provided a cultured cell population deriving from the culturing of cells which express the GCTM-5 epitope or equivalent. Preferably the cultured cell population includes ductal cells, hepatoblasts, embryonic liver foetal cells, liver or hepatic progenitor cells, binary cells, biliary epithelial cells, multi-potential cells which can differentiate to hepatocytes, biliary cells and pancreatic cells and cells of the luminal surfaces of biliary ducts or pancreatic ducts. Preferably the cell is a hepatoblast that has the potential to differentiate to a hepatic or pancreatic stem cell. Preferably the hepatic or pancreatic stem cells are pancreatic, hepatic and liver progenitor cells that have the capacity to proliferate. Preferably the cell is a hepatic or pancreatic stem cell. More preferably, the cell is a hepatic or pancreatic progenitor cell. Most preferably the cell is a proliferating hepatic or pancreatic progenitor cell.

In yet another aspect of the present invention there is provided a use of the cells which express a marker said marker characterized by binding to a GCTM-5 antibody or active fragment thereof of as herein described. The use may be selected from the group including but not limited to, transplantation, ex vivo expansion, reprogramming to generate other cell types and for identifying new therapeutic agents that may affect how these cells live, grow, replicate, differentiate and die. The invention also provides for a use of the marker and the GCTM-5 antibody to target hepatic and pancreatic stem cells, particularly highly proliferating hepatic or pancreatic cancer cells. Antibody such as GCTM-5 antibody conjugated to toxins or to radioisotopes may be used to target proliferating hepatic and/or pancreatic cells to deliver the toxin to the cells or to identify hepatic and/or pancreatic stem or progenitor cells.

In a preferred aspect of the present invention there is provided a method of treating a liver disorder in a patient, said method comprising:
isolating a liver stem cell which expresses a marker said marker characterised by binding to a GCTM-5 antibody or active fragment thereof; and;
transferring the liver stem cell into the patient.

Under normal circumstances, hepatocytes are almost uniformly quiescent. However, on demand, resting hepatocytes are able re-enter the cycle and proliferate for up to 12 doublings per cell. In addition to the regenerative capacity of hepatocytes, the liver possesses a stem cell population that is multipotent and is activated by massive liver necrosis or cirrhosis. These liver stem cells reside in the terminal bile ductules. Oval cells are thought to be the daughter cells of these true stem cells, and also reside in the terminal bile ductule. Oval cells have been shown to differentiate to hepatocyte and bile ductular cells to repopulate diseased liver. The ductal regions are the site of proliferation of these stem cell populations, as they spread and integrate into the surrounding mesenchyma.

Therefore, liver cells can be repopulated by the use of a stem cell capable of differentiating to a liver cell. Preferably the liver stem cell is a hepatoblast. More preferably the liver stem cell is a liver progenitor cell. It is further preferred that the cell is proliferating.

Liver disorders in the present application are generally those disorders that require replenishment or regeneration of liver cells. Such conditions occur in diseases such as primary biliary cirrhosis (PBC), extrahepatic biliary atresia (EHBA) and alcoholic liver disease (ALD).

Preferably cells isolated using any of the methods described above could be directly used in transplantation therapy of patients with liver disease, or they could be subject to expansion ex vivo. Alternatively, the detector or preferably the GCTM-5 antibody may be used to isolate progenitors from other embryonic foetal pediatric or adult tissues, or to isolate progenitors or stem cells from cultures of embryonic stem cells, embryonic germ cells, adult stem cells, or stem or progenitor cells derived by reprogramming of gene expression. In addition to potential uses in transplantation, the detector of the GCTM-5(+) cells or progeny of the GCTM-5 (+) cells may be studied in vitro to identify new targets for protein, nucleic acid, or small molecule therapeutics.

Further preferred cells include the GCTM(+) cells which are further identified by markers including markers of ductal reactive cells such as, but not limited to N-CAM, CK-19, HEA-125, harmonin and Ep-CAM.

In another preferred aspect of the present invention there is provided a method of treating a pancreatic disorder in a patient, said method comprising:
isolating a pancreatic stem cell which expresses a marker said marker characterised by binding to a GCTM-5 antibody or active fragment thereof; and
transferring the pancreatic stem cell into the patient.

Cell replacement therapy for Type I diabetes is attractive, because there is clinical evidence to indicate that islet cell replacement can provide positive benefit. The pancreatic ducts can serve as a facultative stem cell population to replenish duct, exocrine, and islet tissue, following certain types of damage. Accordingly in liver and in pancreas, GCTM-5 antibody marks a ductal cell population capable of serving as a facultative stem cell reserve for repair after cell loss.

In the pancreas, as in the liver, it is possible to isolate subpopulations of ductal cells using GCTM-5 in conjunction with other surface markers for duct cells such as Ep-CAM. These cell populations may be propagated in vitro and assessed for their ability to expand in numbers differentiate along various pancreatic lineages. The cells may also be inoculated into animals whose islet cells have been depleted through various mechanisms, and assessed for their ability to restore normal glucose homeostasis. GCTM-5 in conjunction with other surface markers may be used to isolate pancreatic precursors from cultures of embryonic or adult stem cells.

The pancreatic disorder may be diabetes, pancreatic cancer or any pancreatic condition which involves replacement of pancreatic stem cells.

In both liver and pancreatic disorders such as in liver and pancreatic cancers, the use of the GCTM-5 antibody to deliver immunotoxins to the hepatic and pancreatic stem cells or progenitor cells of highly proliferating liver or pancreatic cancers can be applied. Because the antibody is specific for these cells, accurate targeting of the toxin can be delivered to the cells.

The present invention further provides a method of diagnosing or monitoring a liver or pancreatic disorder in a patient, said method comprising detecting GCTM-5 antigen, epitope or equivalent in a biological sample. Preferably the biological sample is a body fluid sample or a tissue sample.

It is envisaged that the GCTM-5 antigen, epitope or equivalent may be shed or secreted from the cell surface. Accordingly, the levels of the GCTM-5 antigen, epitope or equivalent may indicate the level of liver or pancreatic progenitor activity. Accordingly, the levels of the antigen or epitope or equivalent in blood or other body fluids or tissues, which could be measured by radioimmunoassay, ELISA or other assays based on GCTM-5 antibody or derivative reagents, could be used to diagnose or to monitor progression and treatment of hepatic, pancreatic and other disorders. This would be useful in monitoring progression of cell growth and proliferation after transplantation.

Figure 14:
FIG. 14 shows immunostaining of pancreatic ductal adenocarcinoma cell line CFPAC-1 with antibody GCTM-5. Nuclear counterstain with DAPI. A subset of cells in the culture shows typical surface staining with GCTM-5.

Examination of the expression of the GCTM-5 antigen was made in pancreatic ductal tissue in cell lines derived from pancreatic adenocarcinoma, aggressive malignant tumours derived from the ducts. Indirect immunofluorescence staining of pancreatic adenocarcinoma cell line CFPAC-1 showed that a subpopulation of cells within this cell line stained strongly with GCTM-5. Accordingly, the GCTM-5 antigen recognises a population of pancreatic duct cancer stem cells. (See FIG. 14) The antibody may be useful as a diagnostic or therapeutic agent in the treatment of pancreatic malignancies. The availability of an immortal tumour cell line expressing the GCTM-5 antigen will aid greatly in the purification and identification of the GCTM-5 antigen.

This ability to identify pancreatic cancer cells or actively proliferating liver and pancreatic stem cells using the GCTM-5 antibody provides for the application to remove these cells from suspensions such as bone marrow prior to administration to a patient. GCTM-5 antibody bound to a solid support such as a bead can facilitate the removal of hepatic and/or pancreatic stem cells that are actively proliferating and are potential cancer cells.

As a marker of a stem cell, the GCTM-5 antigen, epitope or equivalent that binds to a GCTM-5 antibody provides a useful target for identification and isolation of stem cells, preferably liver or pancreatic stem cells, more preferably hepatoblasts or cells of the biliary epithelium. The antigen, epitope or equivalent may also be used as a target of protein, nucleic acid or small molecule therapeutic agents for treatment of stem cells.

The antigen, epitope or equivalent reactive with GCTM-5 antibody may be isolated using affinity techniques or other means of protein purification or by expression cloning. The antigen may be used as a target of protein, nucleic acid or small molecule therapeutic agents. GCTM-5(+) precursors or their progeny may also be capable of differentiation into pancreatic or other lineages and may be useful in treatment of other conditions by cell therapy, or they may be used in laboratory research to develop new pharmaceuticals for treatment of a range of disorders.

The present invention also provides compositions including molecules of the present invention, and methods for their use. Preferably, the molecules are selected from the group including: a detector which recognises a marker on a cell said marker characterized by binding to a GCTM-5 antibody or active fragment thereof and preferably including a GCTM-5 epitope or equivalent thereof; a marker characterized by binding to a GCTM-5 antibody or active fragment thereof and preferably including a GCTM-5 epitope or equivalent; agonists of the marker and antagonists of the marker.

In yet another aspect of the present invention, there is provided an agonist which enhances a biological function of a marker on a cell, said marker characterized by binding to a GCTM-5 antibody or active fragment thereof and preferably including a GCTM-5 epitope or equivalent. Preferably the marker is a GCTM-5 antigen or equivalent.

In yet another aspect of the present invention, there is provided an antagonist which inhibits a biological function of a marker on a cell, said marker characterized by binding to a GCTM-5 antibody or active fragment thereof and preferably including a GCTM-5 epitope or equivalent. Preferably the marker is a GCTM-5 antigen or equivalent.

Agonists and antagonists of the marker may provide useful molecules to modulate the function of the marker. The agonists and antagonists may also modulate the function of a cell which expresses the marker on its surface. Such agonists and antagonists may be identified by any method known to those skilled in the art. The method may include, but not be limited to, a competition assay wherein binding to the marker of the agonist or antagonist may inhibit binding of a GCTM-5 antibody or fragment.

In yet another aspect of the present invention, there is provided a composition including a detector which recognises a marker on a sub-population of stem cells, said marker characterized by binding to a GCTM-5 antibody or active fragment thereof and preferably including a GCTM-5 epitope or equivalent, and a pharmaceutically acceptable carrier. Preferably the stem cell is a hepatic stem cell or a pancreatic stem cell. Preferably the detector is a GCTM-5 antibody or fragment.

In yet another aspect of the present invention, there is provided a composition including a marker, said marker characterized by binding to a GCTM-5 antibody or active fragment thereof and preferably including a GCTM-5 epitope or equivalent, and a pharmaceutically acceptable carrier. Preferably the marker is a GCTM-5 antigen. Preferably the marker identifies a sub-population of stem cells. Preferably the stem cell is a hepatic stem cell or a pancreatic stem cell.

In yet another aspect of the present invention, there is provided a composition including an agonist of a marker, said marker characterized by binding to a GCTM-5 antibody or active fragment thereof and preferably including a GCTM-5 epitope or equivalent, and a pharmaceutically acceptable carrier. Preferably the marker is a GCTM-5 antigen or equivalent.

In yet another aspect of the present invention, there is provided a composition including an antagonist of a marker, said marker characterized by binding to a GCTM-5 antibody or active fragment thereof and preferably including a GCTM-5 epitope or equivalent, and a pharmaceutically acceptable carrier. Preferably the marker is a GCTM-5 antigen or equivalent.

The composition may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain additional agents such as suspending, stabilizing and/or dispersing agents. Alternatively, the compositions may be in powder form for reconstitution with a suitable vehicle, e.g., sterile pyrogen-free water, before use.

In particular embodiments, compositions of the present invention may be used to treat a subject. A subject in need of treatment may have a liver disorder or a pancreatic disorder. The provision of antibodies, agonists or antagonists may provide a beneficial outcome to the subject.

In yet another aspect of the present invention, there is provided a method of treating a subject including the step of administering to the subject, an effective amount of a composition, wherein the composition includes a detector which recognises a marker on the cell said marker characterized by binding to a GCTM-5 antibody or active fragment thereof and preferably including a GCTM-5 epitope or equivalent, and wherein the subject has a disorder selected from the group including a liver disorder and a pancreatic disorder. Preferably the detector is an antibody. More preferably the antibody is a GCTM-5 antibody.

In yet another aspect of the present invention, there is provided a method of treating a subject including the step of administering to the subject, an effective amount of a composition, wherein the composition includes an agonist of a marker on the cell, said marker characterized by binding to a GCTM-5 antibody or active fragment thereof and preferably including a GCTM-5 epitope or equivalent, and wherein the subject has a disorder selected from the group including a liver disorder and a pancreas disorder. Preferably the marker is a GCTM-5 antigen or equivalent.

In yet another aspect of the present invention, there is provided a method of treating a subject including the step of administering to the subject, an effective amount of a composition, wherein the composition includes an antagonist of a marker on the cell, said marker characterized by binding to a GCTM-5 antibody or active fragment thereof and preferably including a GCTM-5 epitope or equivalent, and wherein the subject has a disorder selected from the group including a liver disorder and a pancreatic disorder. Preferably the marker is a GCTM-5 antigen or equivalent.

The term "effective amount" means a dosage sufficient to provide treatment or prevention for the disease or condition being treated or prevented. This will vary depending on the subject and the disease/condition being effected. The effective amounts of an agent used in the methods of the present invention may vary depending upon the manner of administration, the condition of the subject to be treated, and ultimately will be decided by the attending scientist, physician or veterinarian.

The agonists and antagonists can be used to deliver components to the specific cells which express the marker. Immunotoxins and radioisotopes may be delivered to the cells via the use of the GCTM-5 antibody to which the agonists and antagonists react.

In yet another aspect of the present invention, there is provided a kit for detecting a cell marker, wherein the kit includes a detector which recognises the marker said marker characterized by binding to a GCTM-5 antibody or active fragment thereof and preferably including a GCTM-5 epitope or equivalent. Preferably the detector is a GCTM-5 antibody or fragment. Preferably the kit may be used to detect the marker in a biological sample. Preferably the biological sample is a body fluid or a tissue sample.

As used herein, the term "biological sample" is intended to encompass cellular and non-cellular biological material, including, but not limited to, cell cultures, tissue cultures, conditioned medium, tissue samples, blood, serum, other bodily fluids and biopsy samples.

In yet a further aspect of the present invention, there is provided a kit for detecting a marker on a sub-population of stem cells, wherein the kit includes a detector which recognises the marker, said marker characterized by binding to a GCTM-5 antibody or active fragment thereof and preferably including a GCTM-5 epitope or equivalent. Preferably the stem cell is a hepatic stem cell or a pancreatic stem cell. Preferably the detector is an antibody. More preferably the antibody is a GCTM-5 antibody or fragment.

The kits may be supplied with instructions to use the detector to identify cells expressing the cell marker, said marker characterized by binding to a GCTM-5 antibody or active fragment thereof and preferably including a GCTM-5 epitope or equivalent. The detector may be contacted to the cells to bind and identify those cells expressing the marker. Bound detector may be identified as described above. Alternatively, the kit may be used to identify marker that has been released into culture media from cells expressing the marker, said marker including the GCTM-5 epitope or equivalent thereof. The amount of marker expressed my indicate the level of proliferation or the amount of liver stem cells present in the sample.

In yet another aspect of the invention there is provided a kit for isolating a subpopulation of stem cells, said kit comprising a detector for detecting cells expressing a marker, said marker characterized by binding to a GCTM-5 antibody or active fragment thereof and preferably including a GCTM-5 epitope or equivalent thereof, and preferably a means to isolate the detector.

The kits may be used to isolate and identify stem cells, preferably hepatic stem cells. More preferably, the hepatic stem cells are hepatoblasts that can differentiate to liver, hepatic or pancreatic stem cells. Most preferably, the kits are used to isolate or identify hepatoblasts.

When isolating the cells, the kits may be supplied with a means to isolate the detector. This will facilitate the isolation of the cells identified, or bound to the detector. For instance, where the detector is an antibody, preferably the GCTM-5 antibody, the antibody may be bound to a solid support such as a bead which can facilitate the isolation of the cell by methods commonly available to the skilled addressee.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed in Australia before the priority date of this application.

Finally it is to be understood that various other modifications and/or alterations may be made without departing from the spirit of the present invention as outlined herein.

EXAMPLES

Example 1

Figure 1B:
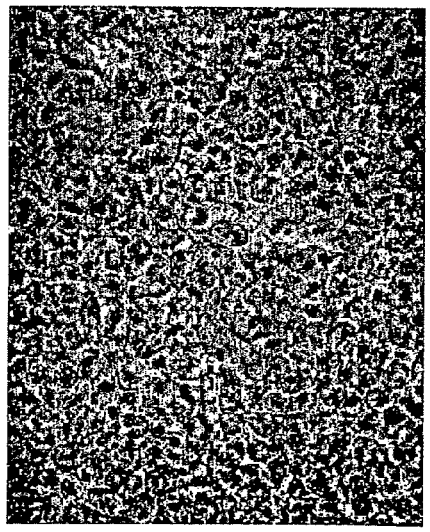

Derivation and Characterisation of Antibodies from Hybridoma Culture (a) Derivation of GCTM-5 Antibody Female BalbC mice of 4-6 weeks of age were immunised with a crude membrane preparation from a testicular seminoma. Fresh tumour tissue was disrupted by Dounce homogenisation, and the homogenate was first subjected to low speed centrifugation at 3,000×g to remove nuclei, mitochondria, cytoskeletal elements and debris, then high speed centrifugation at 100000×g for one hour. The resulting pellet was used for immunisation. Fusion with myeloma cell line NS-1 and subsequent selection of hybridomas was carried out using standard techniques. Hybridoma supernatants were first screened by antibody capture ELISA using the immunising membrane preparation. Secondary screening was performed using either immunocytochemistry on fixed or frozen sections of seminomas, or by indirect immunofluorescence on fixed slides of cultured embryonal carcinoma cell lines including GCT27X-1 (FIG. 1).

(b) Antibody Isotyping

GCTM-5 antibody was isotyped using the ISOStrip Kit (Roche Diagnostics, USA) according to manufacturer's instructions. Briefly, the hybridoma supernatant was diluted 1:20 in calcium/magnesium-free phosphate buffered saline (PBS-, Gibco BRL, Melbourne), and 150 µl of this was added to the ISOStrip tube containing latex beads. This was incubated at room temperature (RT) for 30 seconds, before vortexing to resuspend the latex beads. The ISOStrip strip was placed in the tube and incubated at RT for 5-10 minutes. The latex beads migrate at a controlled rate, relative to the isotype of the antibody in the supernatant which can be read off the strip using the isotype markers.

(c) Cultured Cell Lines

Cell lines GCT27X-1 (human embryonal carcinoma), GCT 44 (primitive endoderm yolk sac carcinoma), GCT 72 and GCT119 (visceral yolk sac carcinoma) were cultured as described in Pera, M. F et al (1987) "Cultured stem cells from human testicular teratomas: the nature of human embryonal carcinoma and its comparison with two types of yolk sac carcinoma", Int. J. Cancer 40, 334-343, and Pera M. F. et al. (1989) "Isolation and characterization of a multipotent clone of human embryonal carcinoma or cells" Differentiation, 42, 10-23. Human embryonic stem cell lines HES-2 and HES-3 were propagated as described by Reubinoff B et al. (2000) "Embryonic stem cell lines from human blastocysts: somatic differentiation in vitro". Nat. Biotechnol. 18, 399-404, and differentiated cells were obtained by cultivation of colonies to high density in situ (Reubinoff B et al. 2000) or by modification of the culture medium. Cell lines HEK293 and HepG2 were propagated as monolayer cultures in Dulbecco's Modified Eagles medium supplemented with 10% fetal calf serum and antibiotics.

(d) Summary of GCTM-5 Expression in Cultured Cell Lines and Isolated Cells

Immunofluorescent analysis identified a number of cell lines which were positive or negative for GCTM-5 expression. Reactivity of the antibody was first noted with a small subpopulation of differentiated cells in cultures of human embryonal carcinoma cell line GCT27X-1. Table 1 shows a summary of the reactivity of the antibody with cultured cell lines, including adult hepatocarcinoma cell line (HepG2), human embryonal kidney (HEK293), and EC cell lines GCT27X-1, GCT44, GCT72 and GCT44 and primary biliary epithelial cells.

Figures 7A, 7B, 7C:
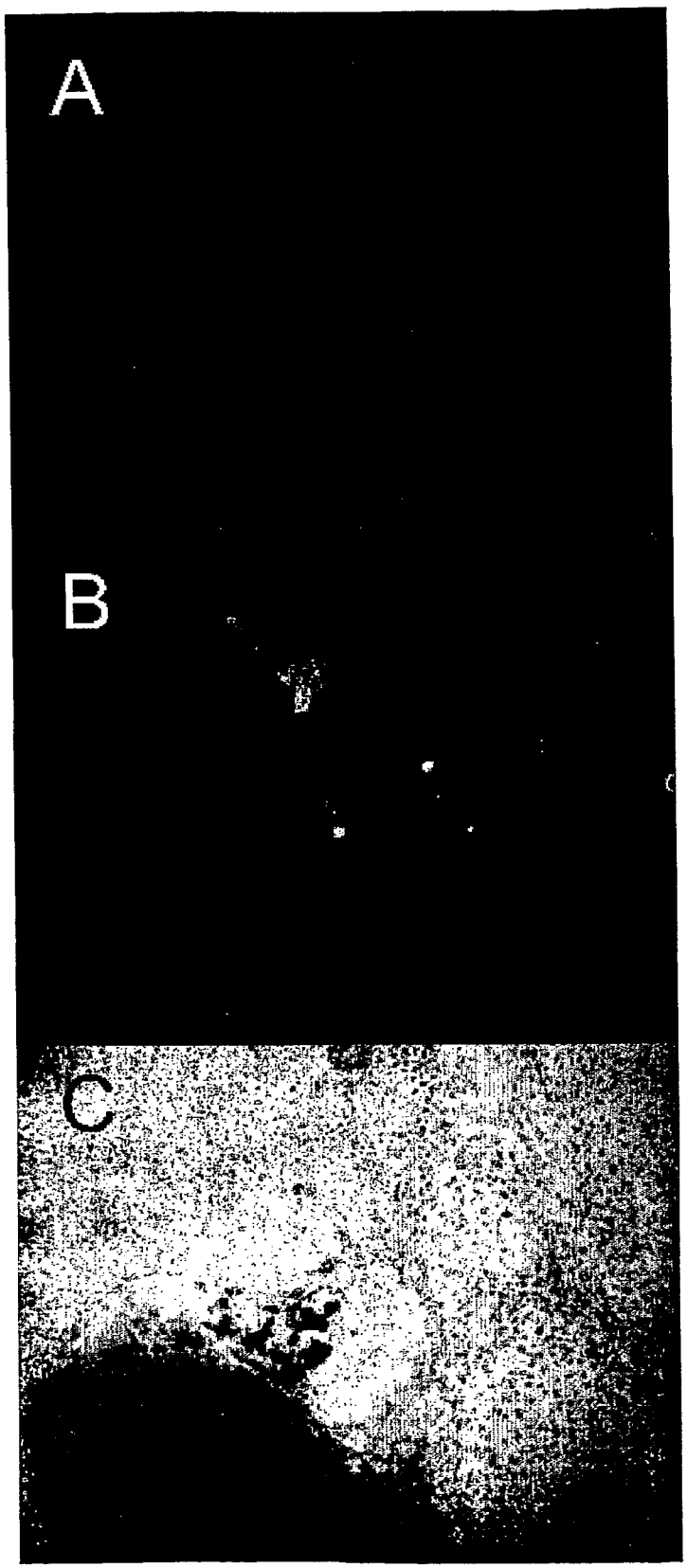
FIG. 7 shows expression of GCTM-5 in differentiating cultures of human pluripotent stem cells. A and B, embryonal carcinoma cell line GCT 27-X1. A shows DNA staining, B shows GCTM-5 immunostaining. C, staining of live cultures of differentiating human embryonic stem cells (HES-3) with GCTM-5; cluster of positive cells in red, hematoxylin counterstain in blue. Magnification 100× on all panels.

Positively stained cells showing a characteristic polygonal morphology were observed consistently in differentiating cultures of human embryonal carcinoma or embryonic stem cells; other permanent cell lines were negative or showed only sporadic reactivity. FIGS. 7A and 7B show DNA staining and immunostaining respectively of a culture of GCT27X-1 cells with GCTM-5 antibody. Fixed preparations of differentiating cultures of embryonic stem cells showed a similar staining pattern in a small minority (<1%) of cells (not shown). Incubation of live cultures of differentiating embryonic stem cells at 4° C. with the antibody prior to fixation revealed that the epitope reactive with the reagent was indeed accessible outside of the cell (FIG. 7C).

(e) Deposit of Hybridoma

The hybridoma which produces the antibody was deposited at the European Collection of Animal Cell Cultures (ECACC) Health Protection Agency, Porton Down, Salisbury, Wiltshire, SP4OJG, United Kingdom on 16 Oct. 2003 and was designated the accession number 03101603.

TABLE 1

GCTM-5 expression analysis in a variety of cultured cell lines & isolated biliary cells.

| Cell Line | Cell Line Description | GCTM-5 Expression |
| --- | --- | --- |
| HepG2 | Hepatocellular carcinoma | − |
| HEK293-T | Human embryonal kidney | − |
| GCT27X-1 | Human embryonal carcinoma | + |
| GCT44 | Primitive Endoderm-like Yolk Sac Carcinoma | − |
| GCT72 | Visceral endoderm-like Yolk Sac Carcinoma | +/− (occasionally positive cells in some cultures) |
| GCT119 | Visceral endoderm-line Yolk Sac Carcinoma | − |
| HES-2 HES-3 | Differentiating cultures of human embryonic stem cells | + |
| Biliary Epithelial Cells | Primary culture | +++ |
| CFPAC-1 | Pancreatic adenocarcinoma | +++ on subpopulation of cells |

GCTM-5 expression: (−), no cells stained; (+), clear positive staining in <1% of cells; (+++), strong expression in majority of cells.

Example 2

Characterisation of Antigen Recognised by GCTM-5 Antibody (a) Immunoblot Analysis of GCTM-5 Antigen Differentiating cultures of human embryonal carcinoma (GCT27X-1) or embryonic cells were grown in 12-well plates. Cells in 4 wells of a plate was lysed with Laemmli sample buffer containing 0.2M dithiothreitol (DTT). A sample of cultured biliary epithelial cells, isolated from a patient with primary biliary cirrhosis using antibody HEA-125 and maintained in primary culture for 10 days, was also lysed into Laemmli sample buffer. The sample was run on a 10% SDS polyacrylamide gel with a BENCHMARK Prestained Protein Ladder (Invitrogen, Victoria). The protein was then transferred to Hybond-P membrane (Amersham Biosciences, Australia) and membrane blotted with GCTM-5 antibody(neat), or CAM5.2 (BD Biosciences, Australia) against CK8 and 18 (BD Biosciences, Melb, Vic, AU) as a positive control for the cell preparation. An anti-mouse Ig conjugated to horse-radish peroxidase (HRP) secondary antibody (Dako, NSW) was added at a dilution of 1:10,000 in TBS-Tween20. Chemiluminescent ECL Reagent (Amersham Biosciences, Australia) was added to the membrane for 5 minutes, before exposure of the membrane to Hyperfilm (Amersham Biosciences, Australia).

(b) Immunohistochemistry

Double immunostaining studies of antigen co-localisation in normal and diseased adult liver tissue was performed using the fluorescent conjugates, Texas Red (IgG1) or Fluorescein isothyocyanate (FITC IgG2a, Cambridge BioScience, Cambridge UK) on 5 µm cryostat sections fixed in acetone as described in Fabris, L. et al. (2000) "Characterisation and isolation of ductular cells co-expressing neural cell adhesion molecule and Bcl-2 from primary cholangiopathies and ductual plate malformations" Am. J. Pathol. 156(4): 1599-1612.

The primary antibody combination consisted of anti-CK-19 (IgG2a, 1:10, Progen, Heidelberg, Germany) or anti-N-CAM (Igb2a, Dako) with GCTM-5 (IgG1, neat supernatant).

Human cell lines including GCT27X-1 embryonal carcinoma cells or human embryonic cells grown on 12-well slides were fixed with 100% ethanol. For indirect immunofluorescent analysis of differentiating human embryonal carcinoma or embryonic stem cell cultures, a combination of primary antibody GCTM-5 antibody (IgG1, neat supernatant) and fluorescein-conjugated secondary antibody, anti-mouse Ig-FITC (1:40, Dako, Australia) was used. Cell nuclei were then stained with 1 µg/ml 4',6-diamidino-2-phenylindole, dihydrochloride (DAPI, Sigma, NSW).

(c) Identification of Cell Surface Localisation of GCTM-5 Antigen

Immunostaining of live differentiating embryonic stem cell cultures five weeks following subculture was achieved by addition of the primary antibody to the cells prior to fixation. The cells were incubated with GCTM-5 antibody for 10 minutes at 4° C. Then cells were gently washed with phosphate buffered saline three times and fixed in cold 100% ethanol for 5 minutes. A 1:50 dilution of anti-mouse Ig conjugated to alkaline phosphatase (Dako) was then added, the sections were washed after 30 minutes in Tris-buffered saline (25 mM Tris, 150 mM NaCl, pH 8), and visualisation of the secondary antibody was achieved using the SIGMA FAST: Fast Red TR/Naphthol AS-MX (Sigma Chemical Company, Sydney, New South Wales, Australia). The sections were counterstained with Mayers' Haemotoxylin.

(d) GCTM-5 Antigen Characterisation

Figure 2:
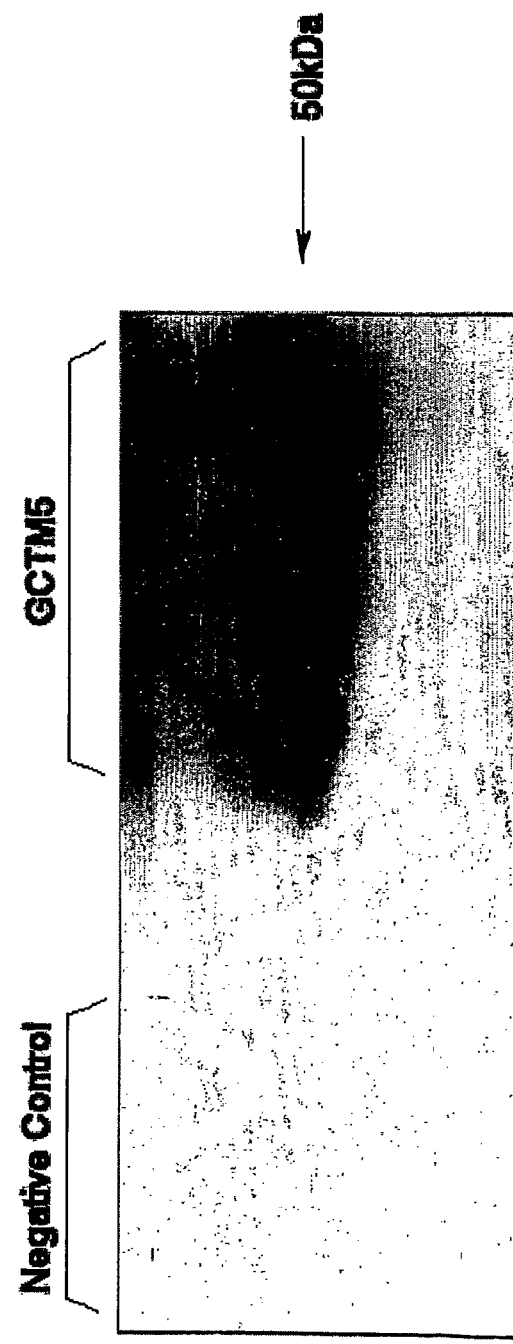
FIG. 2 shows a Western blot of GCTM-5 antigen from differentiated human ES cell cultures.

Western blot analysis on a whole cell lysate of putative endodermal cells revealed a GCTM-5 protein band of approximately 50 kDa (FIG. 2). Lanes probed with the secondary antibody only showed no staining of the 50 kDa band.

Figure 8:
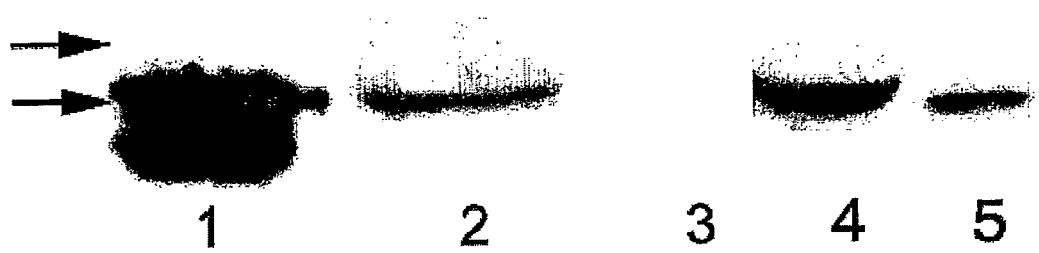
FIG. 8 shows immunoblot of a whole cell lysate of differentiating culture of human embryonal carcinoma cell line GCT 27X-1 probed with GCTM-5, CAM 5.2 against CK 8 and 18, or secondary antibody only; or lysates of biliary epithelial cells and differentiating ES cells probed with GCTM-5. Lane 1, CAM 5.2; lane 2, GCTM-5; lane 3, secondary antibody only; lane 4, biliary epithelial cell lysate probed with GCTM-5; lane 5 differentiating human ES cell lysate probed with GCTM-5. Arrowheads indicate position of 64 and 49 kDa molecular weight markers.

Lanes probed with antibody CAM 5.2 showed bands of the expected sizes of 50 and 43 kDa (FIG. 8, lane 1), while the lane probed with only the secondary antibody showed no staining (FIG. 8, lane 3). Lysates of biliary epithelial cells from a patient with primary biliary cirrhosis (FIG. 8, lane 4) or differentiating human ES cells (FIG. 8, lane 5) also contained bands of 50 kDa reactive with GCTM-5 antibody.

(e) Cell Surface Localisation of GCTM-5

Figure 3:
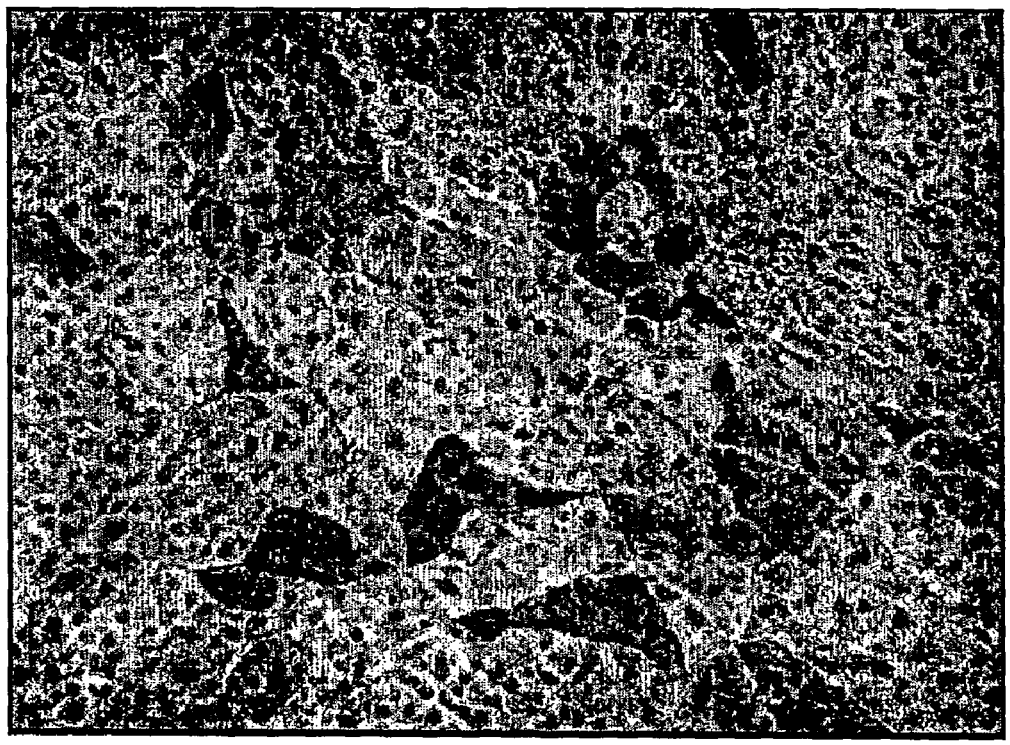
FIG. 3 shows an immunohistochemical analysis of GCTM-5 expression on endodermal cell line; GCTM-5 staining (pink) a subpopulation of these cells. Magnification of 100×.
Figure 4A:
FIG. 4 shows an immunohistochemical analysis of 7 week human fetal tissues revealing GCTM-5 expression exclusively in the liver (A), whilst negative in fetal (B) gut (seen here juxtaposed with positive liver), (C) genital ridge, (D) lung, (E) heart and (F) notochord.
Figure 4B:
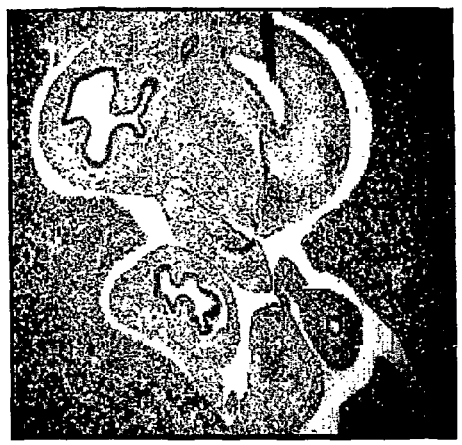
Figure 4C:
Figure 4D:
Figure 4E:
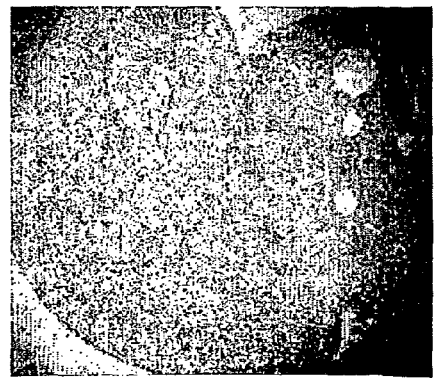
Figure 4F:

The staining pattern observed with GCTM-5 antibody on GCT27X-1 cells was consistent with surface or pericellular staining. Incubation of live cells at 4° C. with the antibody prior to fixation revealed that the epitope reactive with the reagent was indeed localised to the outside of the cell (FIG. 3).

Example 3

Staining of Human Foetal Sections (a) Foetal Tissue

Histological sections of first trimester human embryos were cut from archival material obtained with informed consent from patients undergoing termination of pregnancy at the John Radcliffe Hospital, Oxford, UK. The tissue was fixed in absolute alcohol, embedded in paraffin, and sectioned at 5 µM thickness.

Paraffin embedded human foetal sections for immunohistochemistry were 'de-waxed', fixed and rehydrated. Two 5 minute incubations were made in the citrus-based clearing agent Histolene (Merck, Victoria). The tissue was fixed and rehydrated with two 5 minute incubations in 100% ethanol, followed by 5 minute incubation in 70% ethanol and 5 minutes in running water. The human foetal tissue sections were incubated with neat GCTM-5 antibody supernatant before addition of an anti-mouse Ig conjugated to Alkaline Phosphatase (AP) (Dako, NSW). The visualisation of the secondary antibody involved detection of AP activity with the SIGMA FAST: Fast Red TR/Naphthol AS-MX (Sigma, NSW) substrate and counterstaining with Mayers' Haemotoxylin and 30 mM $(NH_4)OH$.

(b) GCTM-5 Expression Analysis in the Seven Week Human Embryo

The presence of GCTM-5 positive cells in differentiating cultures of human embryonic stem cells suggested that such cells might be found in the developing human embryo. To screen for expression of the marker during human development, sections of first trimester embryos were examined.

Figure 9:
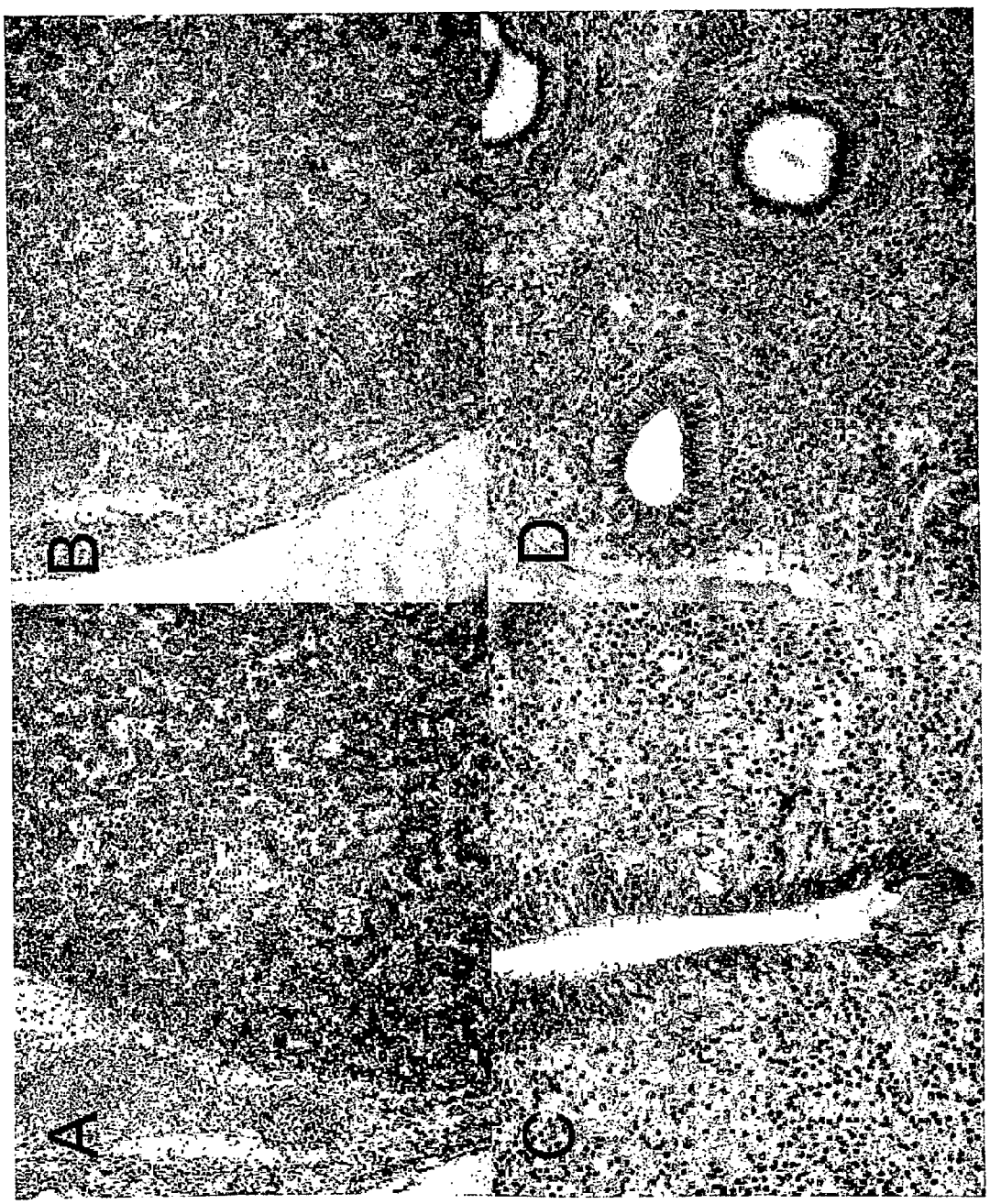
FIG. 9 shows immunohistochemical staining of human embryonic tissue (7 weeks gestation) with GCTM-5. A, liver stained with GCTM-5; B, control for A (no primary antibody); C, neural tube stained with GCTM-5; D, gut loops stained with GCTM-5. Magnification 100× in A and B, 200× in C and D.

Preliminary analysis suggests that GCTM-5 antibody, an antibody raised against a testicular seminoma, reacts with foetal liver. GCTM-5 was expressed exclusively in the liver of the seven week human embryo, in hepatoblasts but not hematopoietic cells, as shown in FIGS. 4 and 9a. GCTM-5 antibody staining was not detected in fetal heart, lung, kidney, central nervous system, and definitive gut (gut and neural tissue, FIGS. 9c and 9d). Significantly, sections of human yolk sac failed to show reactivity with GCTM-5 antibody.

It appears to be expressed uniformly in the hepatoblasts of the developing human foetal liver. Significantly, sections of human yolk sac failed to show reactivity with GCTM-5.

(c) Liver Specific Expression of GCTM-5 in the Human Embryo

Expression analysis in the 7 week human embryo revealed that GCTM-5 is expressed exclusively in the liver. GCTM-5 antibody uniformly stains hepatoblasts of the developing human liver. Hepatoblasts are bipotential cells of the foetal liver which differentiate to give rise to both hepatocytes and biliary cells. This suggests that GCTM-5 antibody recognises an early liver progenitor population, and indicates GCTM-5 antibody and the marker that binds to it could be a useful tool for the further study of early human embryogenesis; in particular liver formation.

(d) GCTM-5 as a Marker for Differentiated Cells Derived from Cultured Pluripotent Stem Cell Lines Previous data identified GCTM-5 expression in very rare populations of cultured human ES cells and EC cell line GCT72.

Staining of live cells with GCTM-5 antibody displayed a typical polygonal pattern of staining. The live staining occurs with cells that are not permeablised, through antibody binding to cell surface or pericellular epitopes. The positive GCTM-5 staining of live cells demonstrates that GCTM-5 antigen is a cell surface marker. This property gives rise to the potential use of this marker to isolate populations of cells by immunomagnetic separation, or fluorescence activated cell sorting (FACS).

Example 4

Diseased Liver Cell Isolation, Culture and Characterisation (a) Liver Tissue

Liver tissue was obtained from the adult and paediatric liver transplant programs at the University & Birmingham Children's Hospitals, NHS Trust Birmingham, UK. Hepatectomy specimens were obtained from Primary Biliary Cirrhosis (PBC, n=6); Alcoholic Liver Cirrhosis (ALD, n=6) and Extra-hepatic biliary atresia (EHBA, n=3). Donor tissue was obtained from the paediatric transplant program when in excess to surgical requirements and served as normal controls (n=5). For immunohistochemistry, tissue was snap frozen and stored at −70° C. For cell isolation, tissue was stored in Dulbecco's Modified Eagles Medium (DMEM, Gibco) at 4° C. and used within 48 h post-hepatectomy.

(b) Diseased Liver Cell Isolation and Culture

Isolation of HEA-125 and GCTM-5-positive cells was based on methodology described in Joplin, R. et al. (1989) "Immunoisolation and culture of biliary epithelial cells from normal human liver", In Vitro Cell Dev. Biol. 25, 1 189-1192; and Crosby, H. et al (2001) "Human hepatic stem-like cells isolated using c-kit or CD34 can differentiate into biliary epithelium" Gastroenterology 120(2): 534-544. Briefly, following percoll density gradient centrifugation at 800 g for 30 min, the non-parenchymal fraction at the percoll band interface and the 1.04 g ml$^{-1}$ layer was removed. The suspension was divided into 2 equal fractions and cells were further purified using immuno-magnetic separation with either the biliary cell marker, Human Epithelial Antigen-125 (HEA-125, 1:10, IgG1, TCS Biologicals Ltd) or GCTM-5 antibody. The antibody-coated cells were then selected using magnetic dynabeads (subclass IgG, Dynal, Wirral, UK).

Isolated cells from each of the fractions were resuspended in biliary plating media and plated in 12×2 cm$^3$ wells (24 well plates) and incubated at 37° C. with 5% CO$_2$. After 24-72 h, media was removed and replaced with biliary cell growth media and re-fed on alternate days.

(c) Phenotypic Characterisation of Cultured Cells

After 6 days, cultured cells were stained for expression of specific proteins. The cells were fixed with 70% v/v ethanol and washed twice with phosphate buffered saline (pH 7.4). Primary antibodies CK-19, (IgG1, 1:100, DAKO, High Wycombe, UK), HEA-125 (IgG1, 1:100) both specific for biliary epithelial cells in liver; CK-18 (IgG1, 1:10, DAKO) recognising both hepatocytes and biliary epithelial cells; CD31 (1:100, Dako) a marker for endothelial cells; and GCTM-5 (IgG1, neat) were incubated for 1 h at 25° C. Staining was visualised using the immunoperoxidase Vector Stain ABC Elite kit (Vector Labs, Peterborough, UK).

d) GCTM-5 Expression in Normal and Diseased Liver

Figure 5:
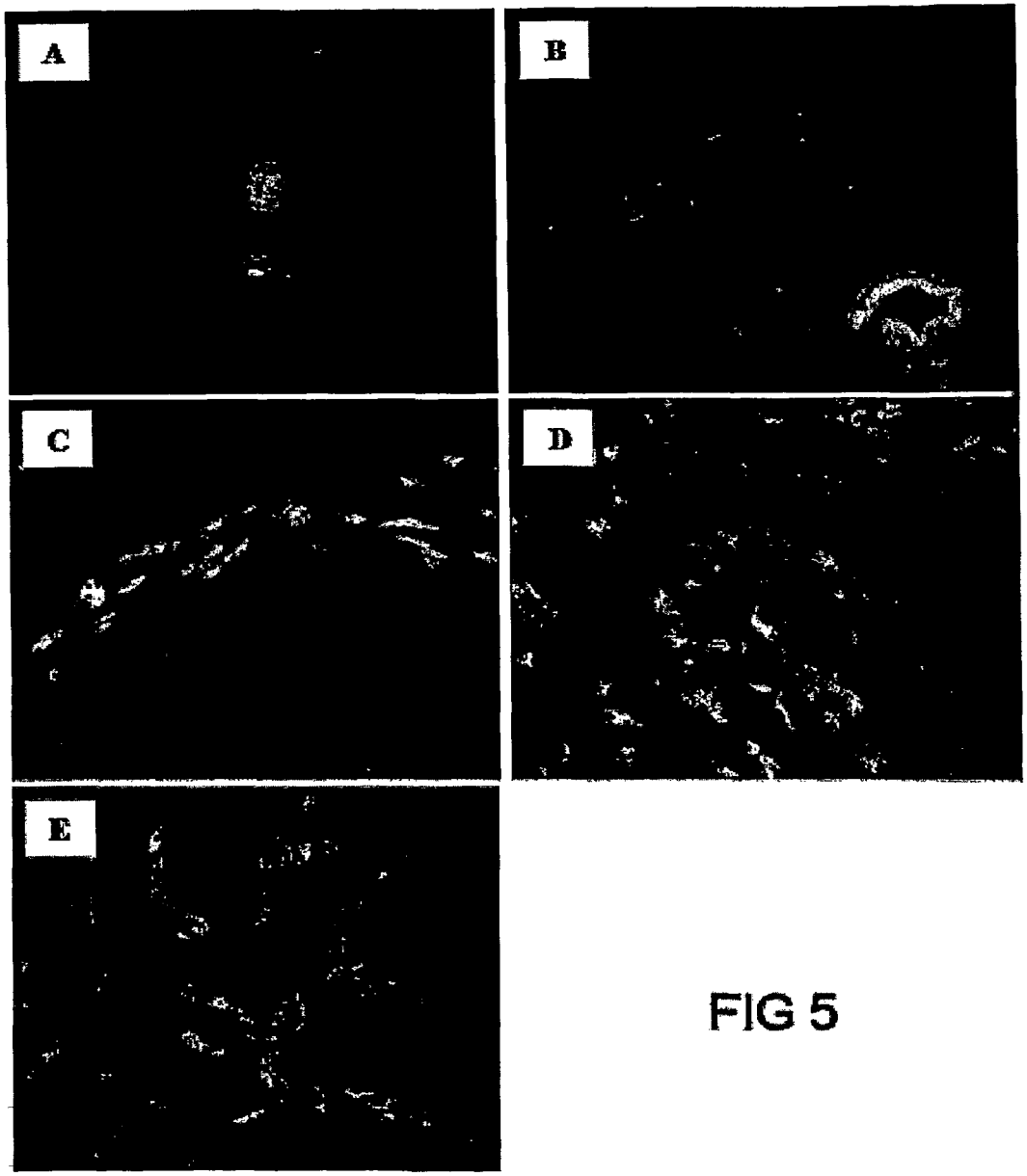
FIG. 5 shows dual fluorescent immunostaining with GCTM-5 (Texas Red) and CK-19 (Fluorescein isothiocyanate) on normal and diseased human liver tissue sections. Bile ducts co-expressed both markers appearing yellow (arrow) in normal (A) and PBC liver (B). The arrowhead shows some CK-19 positive ductular reactive cells in PBC (B). In diseased tissue where ductular reactive cells were present there was some co-localisation of GCTM-5 and CK-19, however cells close to hepatocyte margins were CK-19 positive only (Green, arrowhead). Original magnification ×200.
Figure 6:
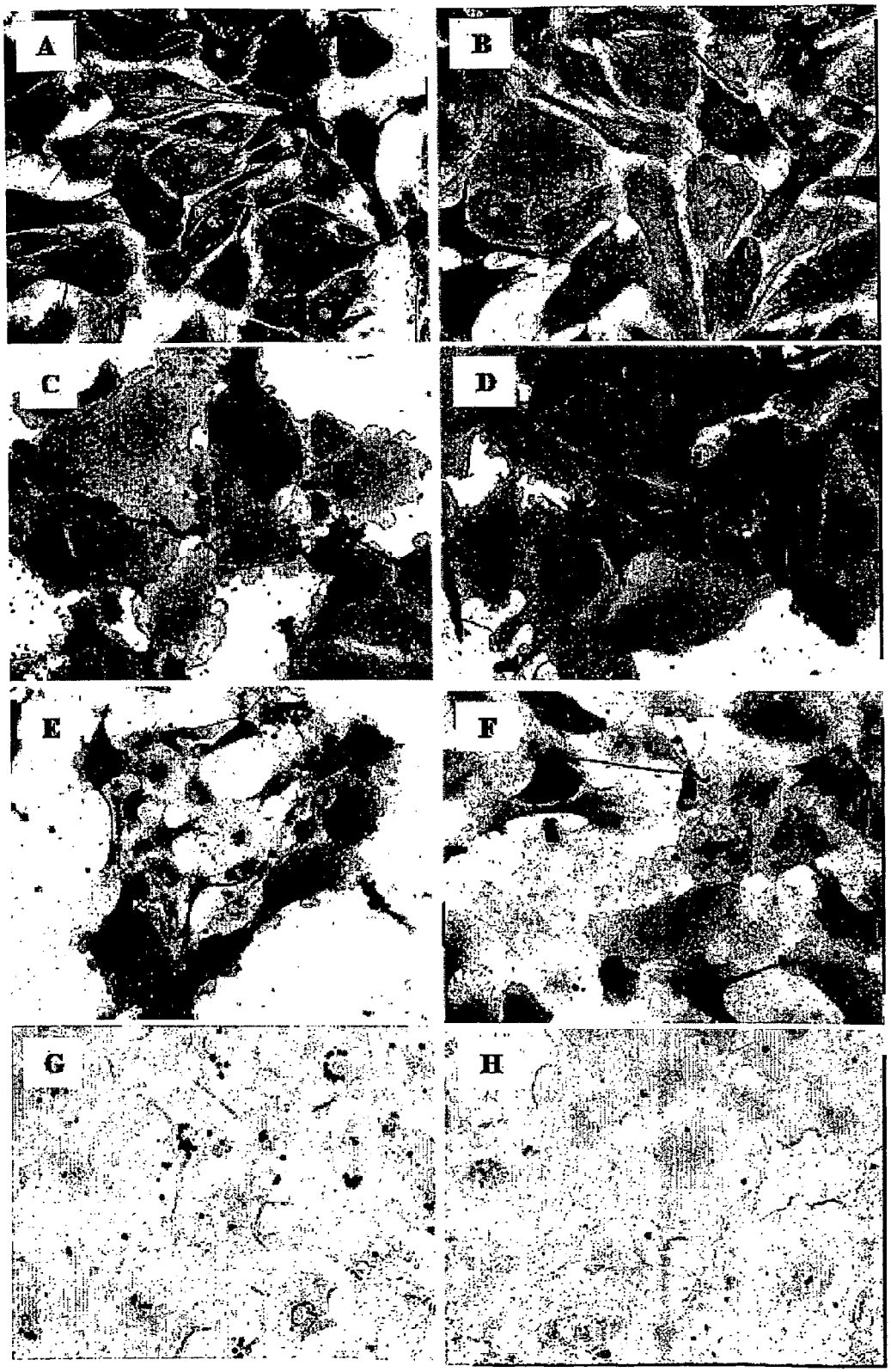
FIG. 6 shows immunocharacterization of GCTM-5 (A, C, E, G) or HEA (B, D, F, H) immunoisolated cells from PBC or ALD liver after 6 days in culture. The GCTM-5 and HEA-isolated cells were remarkably similar to each other expressing BEC phenotype (CK-19 and HEA positive; A-D). Both sets of cells were positive for GCTM-5 (E, F) and negative for the endothelial cell marker, CD31 (G, H). Cells were isolated from PBC (A, B, E-H) and ALD (C,D). Original magnification ×200.

In normal liver (age range 5-34 y), GCTM-5 was present on the luminal surface of bile ducts and co-localisation was present with the biliary cell marker, CK-19 (FIG. 5A). In diseased liver (PBC, ALD), where some intact bile ducts remained, colocalisation with CK-19 and GCTM-5 was again apparent on bile ducts (FIG. 5B, PBC). The ductular reactive cells in all diseased tissue examined (PBC, ALD, EHBA) was similar. GCTM-5 was co-expressed with CK-19 on the majority of the ductular reactive cells (FIG. 5C-E), although some CK-19 positive ductular reactive cells were present closest to the hepatocyte regions.

(e) GCTM-5 Expression in Normal and Diseased Liver

Figure 10:
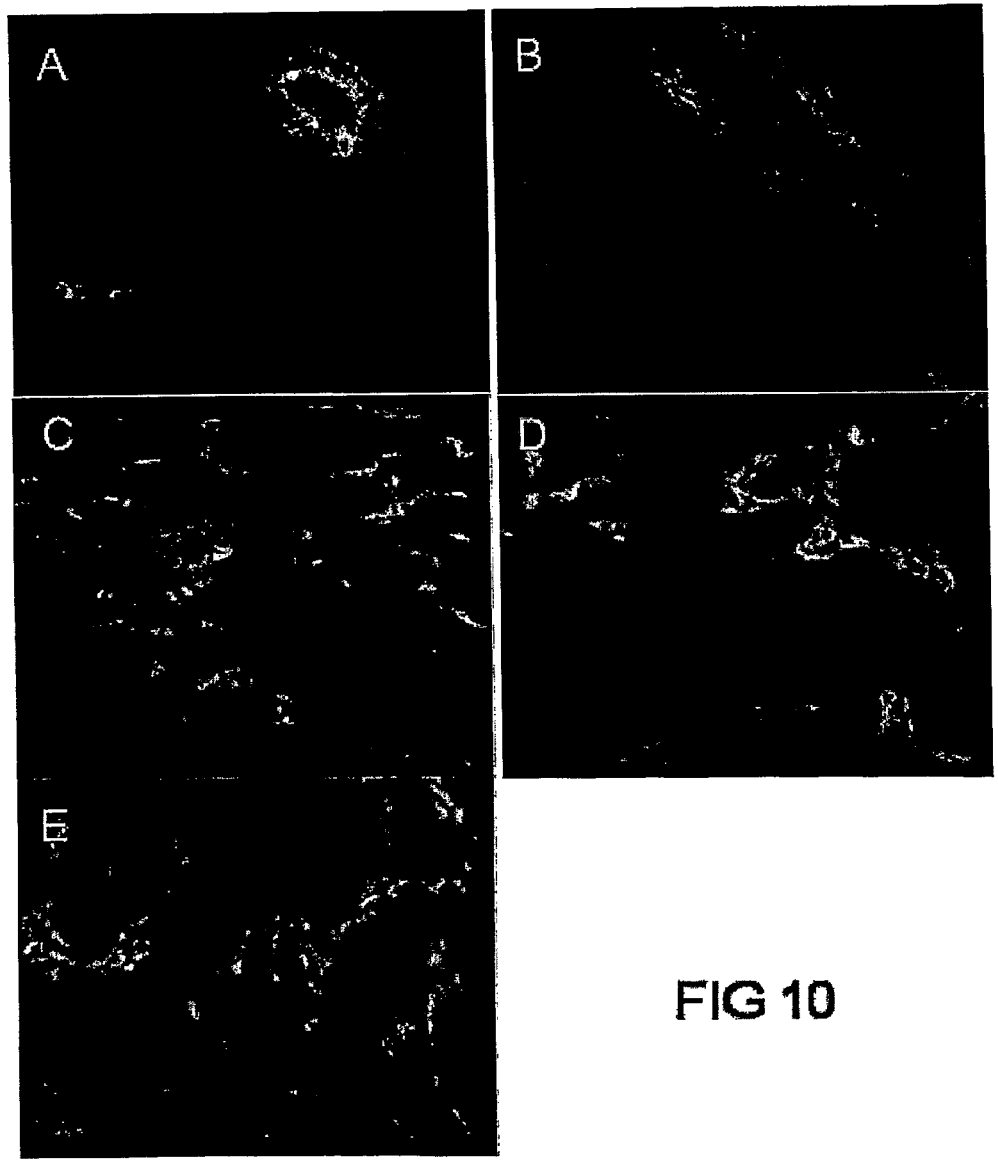
FIG. 10 shows immunolocalisation of GCTM5 on sections of normal and diseased human liver. Tissue was from normal (A), PBC (B,C and E) and EHBA (D) livers. Dual fluorescent immunostaining was carried out with GCTM-5 (Texas Red) and CK-19 (FITC), A-D, and GCTM-5 (Texas Red) and N-CAM (FITC), E. Intact bile ducts co-expressing GCTM-5 and CK19 appear yellow in normal (A) and PBC liver (B). In diseased tissue, some ductular reactive cells co-expressed GCTM-5 with CK19 (B,C; and D) or NCAM (E). Individual cells positive for GCTM-5 only were found in all diseased tissue examined (B, C and D). Magnification 100×, A-C, and 200×, D and E.
Figure 11:
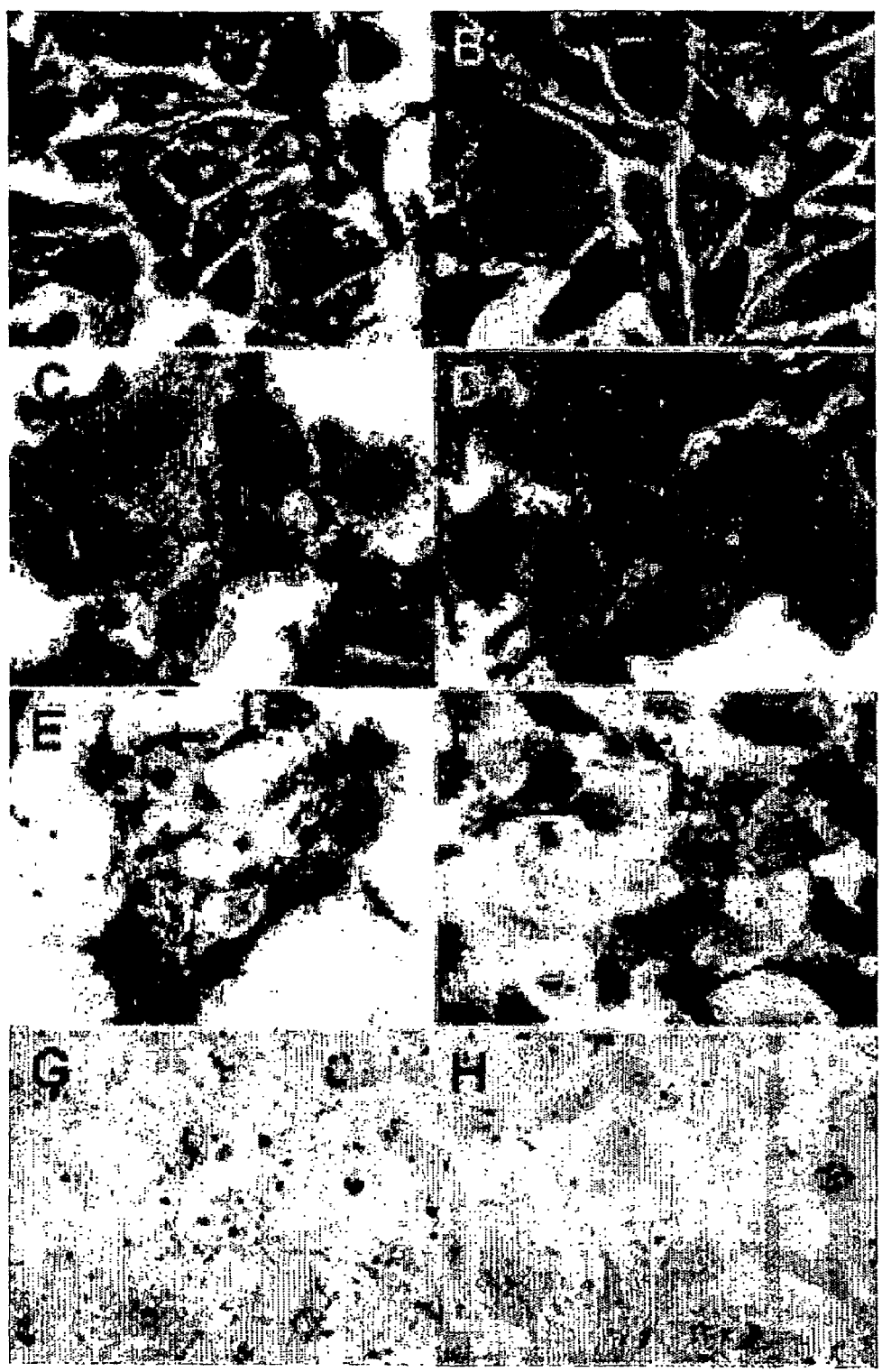
FIG. 11 shows immunocharacterisation of HEA-125 (A, C, E, G) or GCTM5 (B, D, F, H) immunoisolated cells from PBC or ALD liver after 6 days in culture. The GCTM-5 and HEA-isolated cells both expressed a biliary epithelial cell phenotype (CK-19 and HEA positive; A-D) following short term culture. Both sets of cells were positive for GCTM5 (E, F) and negative for the endothelial cell marker, CD31 (G,H). Cells were isolated from PBC (A, B, E-H) and ALD (C,D). Magnification 200×.

In normal liver (age range 5-34 years), GCTM-5 was present on the luminal surface of bile ducts and colocalised with the biliary cell marker, CK-19 (FIG. 10A). Many CK-19 positive cells were negative for GCTM-5. In diseased liver, including PBC and ALD, where some intact bile ducts remained, colocalisation with CK-19 and GCTM-5 antibody was again apparent on the luminal aspect of some of the bile ducts (FIG. 10B, PBC). The pattern of GCTM-5 antibody staining on ductular reactive cells in diseased tissue was particularly noteworthy. GCTM-5 appeared to label only a subpopulation of CK19 positive cells (FIGS. 10C and D). Moreover, a small but discrete number of cells were positive for GCTM-5. only (FIGS. 10B and C). Further immunostaining for N-CAM, another marker reported to label ductular reactive cells specifically (and not cells in intact ducts), revealed a similar pattern of expression. N-CAM displayed some colocalisation with GCTM-5 antibody, but not all cells were co-labelled and there were individual cells positive for GCTM-5 only (FIG. 10E).

(f) GCTM-5 Positive Cells Isolated from Diseased Liver— Phenotype of GCTM-5 Cultured Cells from Cirrhotic Liver The phenotype of cells isolated using GCTM-5 antibody by immunomagnetic separation and growth in culture for 6 days was compared to biliary epithelial cells isolated using HEA-125 from 4 diseased livers (3 PBC and 1 ALD). With time in culture in biliary growth medium, colonies expanded in both groups and gave rise to cultures with remarkably similar properties. When immunostained using the biliary cell markers CK-19 and HEA-125, colonies derived from the isolated GCTM-5 and HEA-125 cells were positive (FIG. 6A-D). All cultured cells stained with CK-18 (data not shown). Both groups of cultured cells stained positive for the GCTM-5 antibody (FIG. 6E,F) but were negative for the endothelial cell marker CD31 (FIG. 6G,H) and a no primary control (data not shown).

(g) GCTM-5 Expression in Diseased Liver

The staining of GCTM-5 antibody in normal and diseased adult liver revealed a pattern of expression which correlates with the previous data showing liver specificity of the marker. The expression of GCTM-5, and its localisation with cytokeratin 19 shows a marker for biliary epithelial cells and ductular reactions in adult liver. GCTM-5 expression was analysed in normal paediatric and adult liver, as well as liver tissue of patients with primary biliary cirrhosis (PBC), extrahepatic biliary atresia (EHBA) or alcoholic liver disease (ALD).

GCTM-5 antibody staining of diseased liver of patients with PBC, EHBA and ALD revealed a localisation to the ductal regions of these tissues. Staining in normal paediatric and adult liver showed a much reduced expression of GCTM-5, in comparison with diseased tissues. This strongly implies that GCTM-5 antibody is recognising an epitope expressed on proliferating liver progenitor cells found predominantly in diseased, regenerating tissue. It is possible that these progenitors are a multipotent population with the ability to differentiate to biliary cells and hepatocyte, upon which GCTM-5 expression is down-regulated.

In addition, the number of cells expressing the GCTM-5 antigen in the liver is increased in various forms of liver disease. Therefore, the GCTM-5 antibody or derivative reagents may find application in diagnostic histopathology of hepatic or other disorders. Furthermore, it is possible that the GCTM-5 antigen might be shed or secreted from the cell surface. Therefore, the levels of the antigen in blood or other body fluids, which could be measured by radioimmunoassay, ELISA or other assays based on GCTM-5 antibody or derivative reagents, could be used to diagnose or to monitor progression and treatment of hepatic and other disorders.

The GCTM-5 is not ideally a marker of cells of hepatocytic origin in the adult liver given its lack of expression in mature hepatocytes and down-regulation of expression on the hepatocyte-duct interface. GCTM-5 is a marker of a bipotential precursor population originating from the inner ductal region, whose expression is down regulated upon maturation to hepatocyte, but not biliary epithelium.

Staining of GCTM-5 positive isolated cells from PBC diseased liver revealed a remarkably similar expression pattern to HEA-125. isolated cells. GCTM-5+ cells expressed mature biliary markers, CK19 and EMA (epithelial membrane antigen) (data not shown), and HEA-125, but did not express CD31, an endothelial marker. This data suggests that GCTM-5 is a marker for maturing biliary epithelial cells.

From the data accumulated in this study, it is feasible to hypothesise that GCTM-5 is an early endoderm marker, which appears to have liver specificity in the early human embryo. GCTM-5 may, in the future be utilized to isolate such endoderm progenitors from differentiating human ES cells, or disease adult liver tissue.

Example 5

GCTM-5 Expression in Pancreatic Tissue

Figure 12:
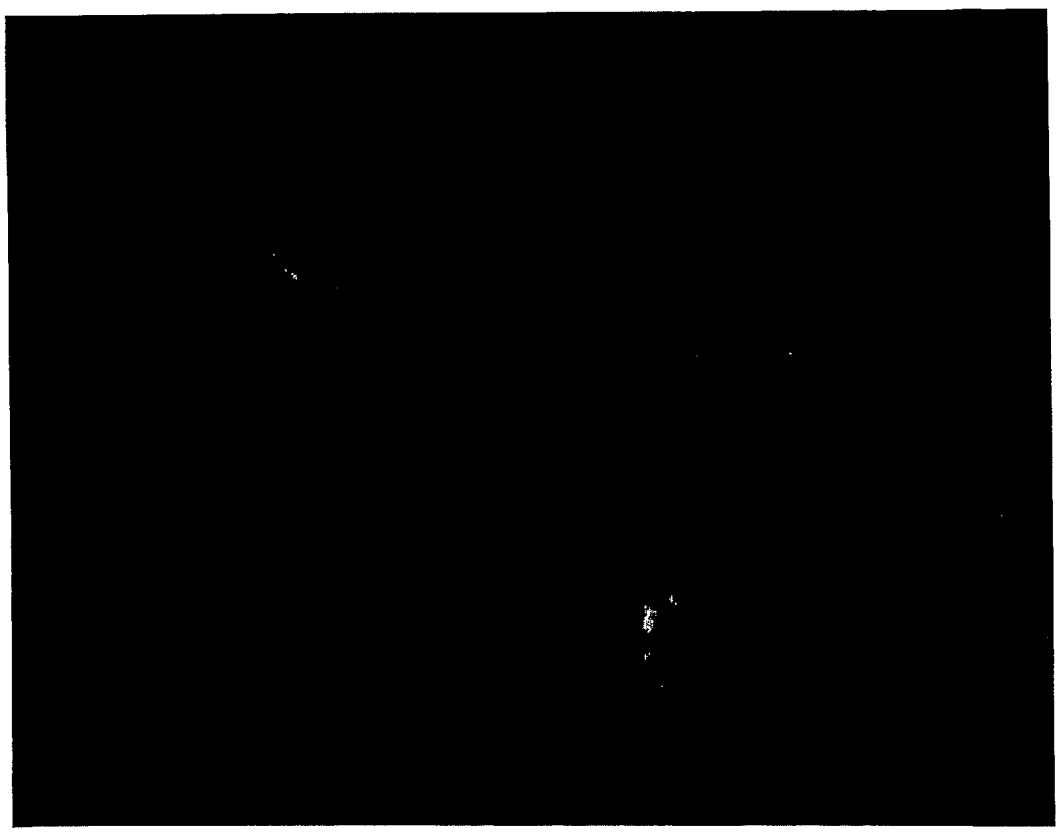
FIG. 12 shows adult human pancreas stained with antibody to harmonin, a protein specifically expressed in all ductal cells.
Figure 13:
FIG. 13 shows the same field as FIG. 12 stained with GCTM-5.

The liver and pancreas are embryologically related, and there is experimental evidence that liver and pancreatic tissue can interconvert through transdifferentiation. Examination of adult pancreatic tissue with the GCTM-5 antibody revealed an interesting pattern of expression. The antigen was absent from the endocrine portion of the pancreas (the islets), and from most of the exocrine tissue (the acinar cells, responsible for secretion of digestive enzymes). However, there was strong staining of areas corresponding to the pancreatic ducts. Colabelling of GCTM-5 positive cells with the pancreatic ductal marker harmonin confirmed the identity of the GCTM-5+ structures, though there were harmonin$^+$, GCTM-5$^-$ cells and harmonin$^-$GCTM-5$^+$ cells. See FIGS. 12 and 13.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the invention.

The invention claimed is:

1. A GCTM-5 antibody produced by a hybridoma having ECACC accession number 03101603, or an antigen-binding portion thereof.

2. The GCTM-5 antibody or an antigen-binding portion thereof according to claim 1 which binds to a hepatic stem cell selected from the group consisting of: a hepatoblast; a hepatic stem cell; a hepatic progenitor cell; a pancreatic stem cell; a pancreatic progenitor cell; a hepatic cancer cell; and a pancreatic cancer cell.

3. The GCTM-5 antibody or an antigen-binding portion thereof according to claim 2 wherein the hepatic stem cell is a cell of the biliary epithelium.

4. The GCTM-5 antibody or an antigen-binding portion thereof according to claim 2 wherein the stem cell is proliferating.

5. A hybridoma that produces a GCTM-5 antibody of ECACC accession number 03101603.

6. A kit for detecting a cell marker, said kit comprising the GCTM-5 antibody or an antigen-binding portion thereof according to claim 1 which is capable of detecting a hepatic stem cell.

7. The kit according to claim 6, wherein the GCTM-5 antibody or an antigen-binding portion thereof is capable of detecting the hepatic stem cell GCTM-5 epitope on a cell selected from the group consisting of: a hepatoblast; a hepatic stem cell; a hepatic progenitor cell; a pancreatic stem cell; a pancreatic progenitor cell; a biliary cell; a biliary epithelial cell; a hepatic cancer cell; and a pancreatic cancer cell.

8. The kit according to claim 6, wherein the GCTM-5 antibody or an antigen-binding portion thereof is capable of detecting the hepatic stem cell GCTM-5 epitope on a cell that is proliferating.

9. The kit according to claim 6, wherein the GCTM-5 antibody or an antigen-binding portion thereof is capable of detecting the hepatic stem cell GCTM-5 epitope in a biological sample including cell culture, tissue culture, conditioned medium, tissue sample, blood, serum, plasma and other bodily fluids and biopsy samples.

10. A kit for isolating a subpopulation of stem cells, said kit comprising the GCTM-5 antibody or an antigen-binding portion thereof according to claim 1 for detecting cells expressing a GCTM-5 epitope, and a means to separate the cells detected by the antigen binding protein.

11. The kit according to claim 10 for isolating a hepatic stem cell selected from the group consisting of: a hepatoblast; a hepatic stem cell; a hepatic progenitor cell; a pancreatic stem cell; and a pancreatic progenitor cell.

12. The kit according to claim 10 for isolating a hepatic stem cell that is proliferating.

13. The kit according to claim 10 for isolating a hepatic stem cell from a biological sample including cell culture, tissue culture, conditioned medium, tissue sample, blood, serum, plasma and other bodily fluids and biopsy samples.

* * * * *